United States Patent
Nathaniel et al.

(10) Patent No.: US 9,433,390 B2
(45) Date of Patent: Sep. 6, 2016

(54) SYSTEM FOR MEASURING THE TRUE DIMENSIONS AND ORIENTATION OF OBJECTS IN A TWO DIMENSIONAL IMAGE

(71) Applicant: ORTHOPEDIC NAVIGATION LTD., Ramat Hasharon (IL)

(72) Inventors: Ram Nathaniel, Tel Aviv (IL); Dan Rappaport, Tel Aviv (IL); Oren Drori, Tel Aviv (IL)

(73) Assignee: SURGIX LTD., Tel Aviv (IL)

( * ) Notice: Subject to any disclaimer, the term of this patent is extended or adjusted under 35 U.S.C. 154(b) by 27 days.

(21) Appl. No.: 14/106,771

(22) Filed: Dec. 15, 2013

(65) Prior Publication Data

US 2014/0180064 A1  Jun. 26, 2014

Related U.S. Application Data

(63) Continuation of application No. 12/665,731, filed as application No. PCT/IL2008/000841 on Jun. 19, 2008, now Pat. No. 8,611,697.

(30) Foreign Application Priority Data

Jun. 21, 2007 (IL) .......................................... 184151

(51) Int. Cl.
*G06K 9/00* (2006.01)
*G06K 9/32* (2006.01)
(Continued)

(52) U.S. Cl.
CPC .............. *A61B 6/12* (2013.01); *G06T 7/0042* (2013.01); *G06T 11/00* (2013.01); *G06T 19/00* (2013.01);
(Continued)

(58) Field of Classification Search
CPC ...... A61B 6/12; A61B 19/54; G06T 7/0042; G06T 2200/04; G06T 2207/10116; G06T 2207/30052; G06T 2207/30204; G06T 2207/10121; G06T 2219/012; G06T 2207/30021
USPC .................. 382/131–132, 286; 600/130, 424
See application file for complete search history.

(56) References Cited

U.S. PATENT DOCUMENTS

| 581,540 A | 4/1897 | Dennis |
| 1,396,920 A | 11/1921 | Brostrom |

(Continued)

FOREIGN PATENT DOCUMENTS

| EP | 0655861 A1 | 5/1995 |
| EP | 1255403 A3 | 3/2004 |

(Continued)

OTHER PUBLICATIONS

B.K.P. Horn and M.J. Brooks, "Shape from Shading" Mid Press, Cambridge Mass (1989).

(Continued)

*Primary Examiner* — Kanjibhai Patel
(74) *Attorney, Agent, or Firm* — Vladimir Sherman; Professional Patent Solutions

(57) ABSTRACT

The invention is a system for measuring the true dimensions and orientation of objects in a two dimensional image. The system is comprised of a ruler comprising at least one set of features each comprised of two or more markers that are identifiable in the image and having a known spatial relationship between them and a software package comprising programs that allow extension of the ruler and other objects in the two dimensional image beyond their physical dimensions or shape. The system can be used together with radiographic imagery means, processing means, and display means to take x-ray images and to measure the true dimensions and orientation of objects and to aid in the identification and location of a surgery tool vs. anatomy in those x-ray images. The invention provides a method of drawing and displaying on a two dimensional x-ray image measurements of objects visible in said image, graphical information, or templates of surgical devices.

24 Claims, 17 Drawing Sheets

(51) Int. Cl.
  *A61B 5/05* (2006.01)
  *A61B 6/12* (2006.01)
  *G06T 7/00* (2006.01)
  *G06T 11/00* (2006.01)
  *G06T 19/00* (2011.01)

(52) U.S. Cl.
  CPC .. *G06T 2200/04* (2013.01); *G06T 2207/10116* (2013.01); *G06T 2207/10121* (2013.01); *G06T 2207/30008* (2013.01); *G06T 2207/30021* (2013.01); *G06T 2207/30052* (2013.01); *G06T 2207/30204* (2013.01); *G06T 2219/012* (2013.01)

(56) References Cited

U.S. PATENT DOCUMENTS

| | | | |
|---|---|---|---|
| 2,819,526 | A | 1/1958 | Brown, Jr. |
| 3,706,883 | A | 12/1972 | McIntyre |
| 3,770,956 | A | 11/1973 | Johnson |
| 3,848,136 | A | 11/1974 | Seldin |
| 4,005,527 | A | 2/1977 | Wilson et al. |
| 4,096,634 | A * | 6/1978 | Gudel ............ 33/475 |
| 4,736,399 | A | 4/1988 | Okazaki |
| 4,890,311 | A | 12/1989 | Saffer |
| 4,915,112 | A | 4/1990 | Singer |
| 4,918,715 | A | 4/1990 | Krupnick et al. |
| 5,052,035 | A | 9/1991 | Krupnick |
| 5,123,056 | A | 6/1992 | Wilson |
| 5,216,700 | A * | 6/1993 | Cherian ............ 378/163 |
| 5,262,856 | A | 11/1993 | Lippman et al. |
| 5,285,785 | A | 2/1994 | Meyer |
| 5,400,513 | A | 3/1995 | Duffield |
| 5,409,004 | A | 4/1995 | Sloan |
| 5,551,160 | A | 9/1996 | Ferris et al. |
| 5,640,436 | A | 6/1997 | Kawai et al. |
| 5,649,032 | A | 7/1997 | Burt et al. |
| 5,687,331 | A | 11/1997 | Volk et al. |
| 5,801,385 | A | 9/1998 | Endo et al. |
| 5,832,422 | A * | 11/1998 | Wiedenhoefer ............ 702/154 |
| 5,833,607 | A | 11/1998 | Chou et al. |
| 5,841,833 | A | 11/1998 | Mazess et al. |
| 5,970,119 | A | 10/1999 | Hofmann |
| 6,075,879 | A | 6/2000 | Roehrig et al. |
| 6,097,833 | A | 8/2000 | Lobregt et al. |
| 6,101,238 | A | 8/2000 | Murthy et al. |
| 6,196,715 | B1 | 3/2001 | Nambu et al. |
| 6,206,566 | B1 | 3/2001 | Schuetz |
| 6,243,439 | B1 | 6/2001 | Arai et al. |
| 6,356,621 | B1 | 3/2002 | Furumori et al. |
| 6,396,903 | B1 | 5/2002 | Wenstrup |
| 6,618,494 | B1 | 9/2003 | Nonay et al. |
| 6,666,579 | B2 | 12/2003 | Jensen |
| 6,792,071 | B2 | 9/2004 | Dewaele |
| 6,925,200 | B2 | 8/2005 | Wood et al. |
| 6,990,229 | B2 | 1/2006 | Ohishi |
| 7,015,906 | B2 | 3/2006 | Olschewski et al. |
| 7,396,161 | B2 | 7/2008 | Schmitt |
| 7,453,977 | B2 | 11/2008 | DiBianca et al. |
| 7,458,977 | B2 * | 12/2008 | McGinley et al. ............ 606/130 |
| 7,499,579 | B2 | 3/2009 | Squilla et al. |
| 7,611,466 | B2 | 11/2009 | Chalana et al. |
| 7,664,298 | B2 | 2/2010 | Lang et al. |
| 7,702,380 | B1 | 4/2010 | Dean |
| 7,773,829 | B1 | 8/2010 | Brandt |
| 7,797,030 | B2 | 9/2010 | Lahm et al. |
| 7,871,406 | B2 | 1/2011 | Nields et al. |
| 7,877,128 | B2 | 1/2011 | Schwartz |
| 7,905,924 | B2 | 3/2011 | White |
| 7,995,822 | B2 | 8/2011 | Lang et al. |
| 8,090,166 | B2 | 1/2012 | Rappaport et al. |
| 8,104,958 | B2 | 1/2012 | Weiser et al. |
| RE43,282 | E | 3/2012 | Alexander et al. |
| 8,311,791 | B1 | 11/2012 | Avisar |
| 8,463,006 | B2 | 6/2013 | Prokoski |
| 8,611,697 | B2 | 12/2013 | Nathaniel et al. |
| 8,657,781 | B2 | 2/2014 | Sewell et al. |
| 8,855,390 | B2 | 10/2014 | Bismuth et al. |
| 9,063,635 | B2 | 6/2015 | Hart et al. |
| 9,109,998 | B2 | 8/2015 | Nathaniel et al. |
| 9,111,180 | B2 | 8/2015 | Rappaport et al. |
| 2002/0077540 | A1 | 6/2002 | Kienzle, III |
| 2003/0014034 | A1 | 1/2003 | Strobel |
| 2004/0034298 | A1 | 2/2004 | Johnson et al. |
| 2004/0086082 | A1 | 5/2004 | Foos et al. |
| 2004/0111024 | A1 | 6/2004 | Zheng et al. |
| 2005/0032028 | A1 | 2/2005 | Chosack et al. |
| 2005/0104018 | A1 | 5/2005 | Chang et al. |
| 2005/0213849 | A1 | 9/2005 | Kreang-Arekul et al. |
| 2006/0120583 | A1 | 6/2006 | Dewaele |
| 2006/0154198 | A1 | 7/2006 | Durbin et al. |
| 2006/0177150 | A1 | 8/2006 | Uyttendaele et al. |
| 2007/0041508 | A1 | 2/2007 | Tubbs |
| 2007/0134637 | A1 | 6/2007 | Bronstein et al. |
| 2008/0056547 | A1 | 3/2008 | Kokubun et al. |
| 2008/0111831 | A1 | 5/2008 | Son et al. |
| 2008/0118023 | A1 | 5/2008 | Besson |
| 2008/0242971 | A1 | 10/2008 | Klingenbeck-Regn |
| 2009/0018808 | A1 | 1/2009 | Bronstein et al. |
| 2009/0059018 | A1 | 3/2009 | Brosnan |
| 2009/0221908 | A1 | 9/2009 | Glossop |
| 2009/0310845 | A1 | 12/2009 | Ogawa et al. |
| 2010/0135467 | A1 | 6/2010 | King et al. |
| 2010/0178644 | A1 | 7/2010 | Meglan et al. |
| 2010/0232670 | A1 | 9/2010 | Blanchard et al. |
| 2011/0019884 | A1 | 1/2011 | Blau |
| 2011/0102461 | A1 | 5/2011 | Schultz et al. |
| 2011/0188726 | A1 | 8/2011 | Nathaniel et al. |
| 2012/0059248 | A1 | 3/2012 | Holsing et al. |
| 2013/0211244 | A1 | 8/2013 | Nathaniel |
| 2013/0322726 | A1 | 12/2013 | Nathaniel |

FOREIGN PATENT DOCUMENTS

| | | |
|---|---|---|
| EP | 1498849 A2 | 1/2005 |
| EP | 1632181 B1 | 11/2007 |
| EP | 2179397 B1 | 8/2014 |
| WO | WO2006114721 A2 | 11/2006 |
| WO | WO2009022266 A1 | 2/2009 |
| WO | WO2011042832 A1 | 4/2011 |

OTHER PUBLICATIONS

Harris, J.H., "The normal cervical spine" (1987). (Web-link: http://rapidshare.comffiles/213791249/TheNormalCervicalSpine.pdf.html).

Segonne, Florent, "Segmentation of Medical Images underTopological Constraints", 2005, USA.

Maintz, et al.; "A Survey of Medical Image Registration"; 1998; pp. 1-37; pp. 1-3, 7-142; The Netherlands.

Russakoff, et al., "Fast Intensity-based 2D-3D Image Registration of Clinical Data Using Light Fields", 2003, pp. 1-7, USA.

Chen, et al., "Automatic Extraction of Femur Contours from Hip X-ray Images", 2005, pp. 1-10, Singapore.

Kass, et al., "Snakes: Active Contour Models", 1988, pp. 321-331. The Netherlands.

Long, et al., "Segmentation and feature extraction of cervical spine x-ray images", 1999, pp. 1037-1046, USA.

Zitova, et al., "Image registration methods: a survey", 2003, pp. 977-1000, Czech Republic.

Lee, et al., "Image Morphing Using Deformation Techniques", 1996, pp. 3-23, Korea.

Parkinson, et al., "Methodological principles for factual analysis of trabecular bone", 2000, pp. 134-142, Australia.

Seraets, et al., "The Radiographic Trabecular Pattern of Hips in Patients With Hip Fractures and in Elderly Control Subjects", 1998, pp. 165-173, The Netherlands.

Geraets, et al., "Analysis of the radiographic trabecular pattern", 1991, pp. 575-581, The Netherlands.

Dougherty, et al., "Lacunarity analysis of spatial pattern in CT images of vertebral trabecular bone for assessing Dsteoporosis", 2002, pp. 129-138, Kuwait.

(56) References Cited

OTHER PUBLICATIONS

Behiels, et al, "Evaluation of image features and search strategies for segmentation of bone structures in radiographs using Active Shape Models", 2002, pp. 47-62, Belgium.
Lum, et al., "Cominging Classifiers for Bone Fracture Detection in X-ray Images", 2005, pp. 1149-1152, Singapore.
Cocosco, et al., "BrainWeb: Online Interface to a 3D MRI Simulated Brain Database", 1997, S425-27, Canada.
Maintz, et al.; "An Overview of Medical Image Registration Methods"; 1998; pp. 1-22; The Netherlands.
Joskowicz L et al: "Long Bone Panoramas From Fluoroscopic X-Ray Images", IEEE Transactions on Medical Imaging, IEEE Service Center, Piscataway, NJ, US, vol. 23, No. 1, Jan. 1, 2004, pp. 26-35, XP011104510, ISSN: 0278-0062, DOI: D01:10.1109/TMI.2003.819931.
Peter Messmer et al: "Image Fusion for Intraoperative Control of Axis in Long Bone Fracture Treatment", European Journal of Trauma, Urban & Vogel, MU, vol. 32, No. 6, Dec. 1, 2006, pp. 555-561, XP019462173, ISSN: 1615-3146, DOI: DOI:10.1007/S00068-006-5159-5.
Foley, et al: "Virtual fluoroscopy", Operative Techniques in Orthopaedics, Saunders, Philadelphia, PA, US, vol. 10, No. 1, Jan. 1, 2000, pp. 77-81, KP005183642, ISSN: 1048-6666, DOI:10.1016/S1048-6666(00)80046-4.
Brodke D et al: "Image guidance for spinal surgery", Operative Techniques in Orthopaedics, Saunders, Philadelphia, PA, US, vol. 13, No. 3, Jul. 1, 2003, pp. 152-158, XP004677528, ISSN: 1048-6666, DOI: 10.10161S1048-6666(03)00020-X.
Amir Herman et al: "Computer-assisted surgery for dynamic hip screw, using Surgix, a novel intraoperative juiding system", The International Journal of Medical Robotics and Computer Assisted Surgery, vol. 5, No. 1, Mar. 1, 2009, pp. 45-50, XP055133701, ISSN: 1478-5951, DOI: 10.1002/rcs.231.
PCT International Search Report issued in PCT Application PCT/IL2008/000841, dated Nov. 3, 2008 (3 pages).
Chinese Patent Office Communication for corresponding Chinese Patent Application No. 200880103240.7, mailed Dec. 23, 2011 (5 pages.
Chinese Patent Office Communication for corresponding Chinese Patent Application No. 200880103240.7, mailed Nov. 16, 2012 (4 pages).
Chinese Patent Office Communication for corresponding Chinese Patent Application No. 200880103240.7, mailed May 2, 2013 (3 pages).
European Search Report issued in European Application EP 14166253.6, mailed Aug. 18, 2014 (9 pages).

\* cited by examiner

© 1998, SMITH & NEPHEW $$TAD = (X_{ap} x \frac{D_{true}}{D_{ap}}) + (X_{lat} x \frac{D_{true}}{D_{lat}})$$

Mosby, Inc. items and derived items copyright © 2003, Mosby, Inc. All rights reserved.

SYSTEM FOR MEASURING THE TRUE DIMENSIONS AND ORIENTATION OF OBJECTS IN A TWO DIMENSIONAL IMAGE

FIELD OF THE INVENTION

The invention is related to the field of medical radiography. More specifically the invention relates to devices and methods of accurately measuring the dimensions in a specific orientation of objects observable in two-dimensional images, e.g. radiographic images.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright whatsoever.

BACKGROUND OF THE INVENTION

The technical problem that is addressed by the present invention has been known since the earliest application of x-rays as an aid in medical diagnostics and the performance of medical procedures. The problem is easily understood with reference to FIG. 1A and FIG. 1B. X-ray source 10 is roughly a point source that emits a cone of x-rays that project an image 40 of radiopaque object 20 on surface 30. Surface 30 is in some cases essentially planar but is usually distorted as a result of the configuration of the equipment used to make the images. The surface 30 can be of any type made sensitive to x-rays, e.g. a sheet of glass or plastic or a thin paper or plastic film coated with a material that fluoresces when struck by x-rays or coated with a photographic emulsion or an electronic device whose surface has an array of pixels such as a CCD device. As can be seen in the Figures, the scale of image 40 on surface 30 depends on the distance of identical objects 20 from the source 10 (FIG. 1A) and/or on the angle of the object with reference to planar surface mentioned parameters. In the absence of this information, time consuming trial and error is needed to complete the procedure and the lack of accurate measurements has been determined to be one of the causes of failures of orthopedic procedures.

As mentioned above, this problem was recognized very early in the development of the field of medical radiography. In January 1897, only a little over one year after the ground breaking paper by Roentgen that gave the first scientific explanation of the phenomenon that he called x-rays, a patent application that eventually became U.S. Pat. No. 581,540 was filed in the U.S. Patent Office. The invention comprises a grid of radiopaque wires placed between the object being x-rayed (inside a human body) and the planar surface on which the images are recorded and an "angle plate" which is applied to the body to insure parallelism of the x-rays. The object of the invention being to provide "an improved radiographic apparatus whereby the exact location of an invisible object, not permeable or difficulty permeable by the so-called "Roentgen" or "X" rays, may be accurately ascertained and measurements made by which operations necessary for the removal of such objects are controlled and guided".

In the intervening years since the publication of U.S. Pat. No. 581,540 and the present, numerous patents have been granted and scientific articles published that provide different solutions to different aspects of the same problem. A brief review of some of these solutions can be found by reviewing the following patents:

U.S. Pat. No. 1,396,920 describes an indicator comprising radiopaque marks on a plane parallel to the object to be observed and the x-ray sensitive plate. In this way the indicator appears on the x-ray image and the known distances between the marks can be used to determine the correct scale of the distances that appear in the image and thus the size of the object can be accurately determined U.S. Pat. No. 5,970,119 describes a scaling device comprising an easily observable radiopaque member having radiolucent gaps spaced a known distance apart. The embodiments of the scaling device can be use externally or incorporated into a catheter to allow the device to be manipulated into a position in the vicinity of the anatomical structure to be measured as close as possible to the plane of the structure while being oriented as closely as possible to perpendicular to the x-ray beam.

U.S. Pat. No. 5,052,035 describes a device comprised of a transparent substrate on which is created a grid of parallel radiopaque lines. The film is placed over the area of the body of the patient of interest and an x-ray image is taken. The grid appears in the x-ray image as an overlay on the anatomical structure. The transparent substrate is adapted so that, by use of a marking instrument, marks can be applied to the body. In this way features that appear in the x-ray image can be accurately located on/in the body of the patient.

U.S. Pat. No. 3,706,883 describes an elongated probe (catheter) that includes at least one radiopaque segment of known length. The probe is introduced into the body and is brought into proximity to the object to be measured. The radiopaque portion of the probe appears on the x-ray image next to the object whose size is unknown. The ratio of the apparent length of the radiopaque portion of the probe to its known length provides the scale factor necessary to determine the length of the other objects that appear in the x-ray image.

U.S. Pat. No. 4,005,527 describes a depth gauge comprised of alternating sections of radiopaque and radiolucent material of known length. The depth gauge can be inserted into a hole or cavity to be observed using x-ray methods. The gauge will be seen on the x-ray image and can be used to provide a scale to measure the depth of the hole and dimensions of other features seen in the image. In one embodiment, the depth gauge is the shaft of a drill and serves to enable the surgeon to know the depth of the hole that he has drilled into a bone.

This brief survey of the prior art gives an indication of a fact of life that is well known to surgeons, i.e. that the solution to the problems first recognized in the earliest days of medical radiography has not yet been found. Each of the solutions proposed to date, while it might represent an improvement over prior proposals or may give adequate results for certain procedures, has not provided an overall solution.

A surgeon using any of the previous measurement techniques, whether involving using a regular ruler to measure objects directly (not through x-ray) or measuring objects on the image itself will experience the same limitations. Measuring objects directly is often problematic since access is limited to the objects measured and measuring on the image itself, besides requiring a calibration, can only provide measurements on the projection of the object and in the projection plane.

While x-ray images are two dimensional and prior art techniques allow reasonably accurate two dimensional measurements in the plane of the image itself, the surgeon would ideally like to have the ability to make three dimensional measurements and measure the objects at any direction he desires. In particular orthopedic surgeons would like to be able to accurately measure objects not in the image plane and to measure objects, without penetrating them, while retaining the measurement accuracy.

It is therefore a purpose of the present invention to provide a ruler which improves upon and overcomes the limitations of prior art rulers used for measuring distances in radiographic images.

It is another purpose of the present invention to provide a ruler which allows a surgeon to make three dimensional measurements and measure objects in a radiographic image at any direction he desires.

It is another purpose of the present invention to provide a ruler which allows a surgeon to accurately measure objects not in the image plane, while retaining the measurement accuracy.

It is another purpose of the present invention to provide a ruler which allows a surgeon to accurately measure objects without penetrating them, while retaining the measurement accuracy.

Further purposes and advantages of this invention will appear as the description proceeds.

SUMMARY OF THE INVENTION

In a first aspect, the invention is a system for measuring the true dimensions and orientation of objects in a two dimensional image. The system is comprised of a ruler comprising at least one set of features each comprised of two or more markers that are identifiable in the image and having a known spatial relationship between them and a software package comprising programs that allow extension of the ruler and other objects in the two dimensional image beyond their physical dimensions or shape.

In embodiments of the invention the markers in each set are arranged in one or more rows having a known spatial relationship between them. If there is more than one of the sets, at least some of the sets are aligned in a direction non-parallel to the measurement direction or to each other.

Embodiments of the system are adapted to measuring x-ray images. Embodiments of the system are adapted to enable it to be used for measuring the true dimensions and orientation of objects and for aiding in the identification and location of a surgery tool vs. anatomy in a radiographic image.

In a second aspect, the invention is an apparatus adapted to enable it to take x-ray images and to measure the true dimensions and orientation of objects and to aid in the identification and location of a surgery tool vs. anatomy in those x-ray images. The apparatus comprises:
a. a system comprising one or more rulers and a software package according to the first aspect of the invention;
b. radiographic imagery means;
c. processing means; and
d. display means
   characterized in that the software package comprises programs that allow the processing means to recognize the features of the ruler on the radiographic image and to use the features to create a virtual extension of the at least one ruler and to draw the virtual extension of the at least one ruler on the radiographic image as an overlay, thereby enabling the user who is pointing the at least one ruler and looking at the radiographic image to accurately measure objects that appear in the radiographic image.

In embodiments of the invention the software package comprises a program that allows the zero scale on the virtual extension of the ruler to be dragged and moved around at will. In other embodiments, if a three dimensional ruler is used to determine a measuring plane and a feature known to be on the measuring plane, then the software package comprises a program that allows the processing means to measure the angle between two lines projected on the measuring plane.

In embodiments of the invention the software package comprises a program that allows the processing and display means to provide real time visualization by using either a one or a three dimensional ruler in order to draw how at least how a part of the result of the operation will look given the positioning of the ruler or some other surgical tool visible in the image.

In embodiments of the invention the software package comprises a program that allows the processing and display means to find markers in the image and place templates of implants or other objects on the image.

In embodiments of the invention the software package comprises a program that allows the processing means to automatically determine the location of a surgical tool in the image and to apply an image enhancement algorithm that automatically concentrates on the specific area of interest to the surgeon.

In embodiments of the invention the software package comprises a program that allows the processing and display means to synchronize AP and axial images.

In a third aspect the invention is a ruler for use in the system of the first and second aspects. The ruler has at least one set of features each comprised of two or more markers that are identifiable in the image having a known spatial relationship between them. In embodiments of the invention the markers in each set are arranged in one or more rows having a known spatial relationship between them and, if there is more than one of the sets, at least some of the sets are aligned in a direction non-parallel to the measurement direction or to each other.

The ruler can be a hand-held ruler used to "point and "measure". The ruler may comprise means for slideably attaching it to a tool. The ruler may be an integral part of a tool, made by making at least part of the tool from a translucent material and embedding opaque markers into it. The ruler may be comprised of small radiopaque markers, with a known spatial relationship between them, embedded in a radiolucent envelope.

In a fourth aspect the invention is a method of drawing and displaying on a two dimensional x-ray image measurements of objects visible in said image, graphical information, or templates of surgical devices. The method comprises the steps of:
a. identifying the location and orientation of at least one known object; and
b. drawing and displaying the measurements, graphical information, or templates on the x-ray image on the basis of the location and the orientation of the known object.

The method is characterized in that the measurements, graphical information, or templates are not a part of the known object. The known object can be a ruler according to the third aspect of the invention, a surgical tool, or an anatomical feature.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

The invention is a system that can be used for measuring the true dimensions in a specific orientation of objects in two and three dimensional images. In order to illustrate the invention and in preferred embodiments thereof, the images considered herein are radiographic images, in particular x-ray images, wherein by x-ray images are meant radiographic images, fluoroscopic images, digital fluoroscopy images, or images taken using any other type that uses x-rays to obtain them. However it is to be understood that the device and methods of the invention can be used in any imaging situation. In the case of x-ray radiography, the device and system of the invention are used to measure the true dimensions and orientation of objects that appear in the image and to aid the surgeon in the identification and location of surgery tools vs. anatomy in the radiographic image.

Figure 16:
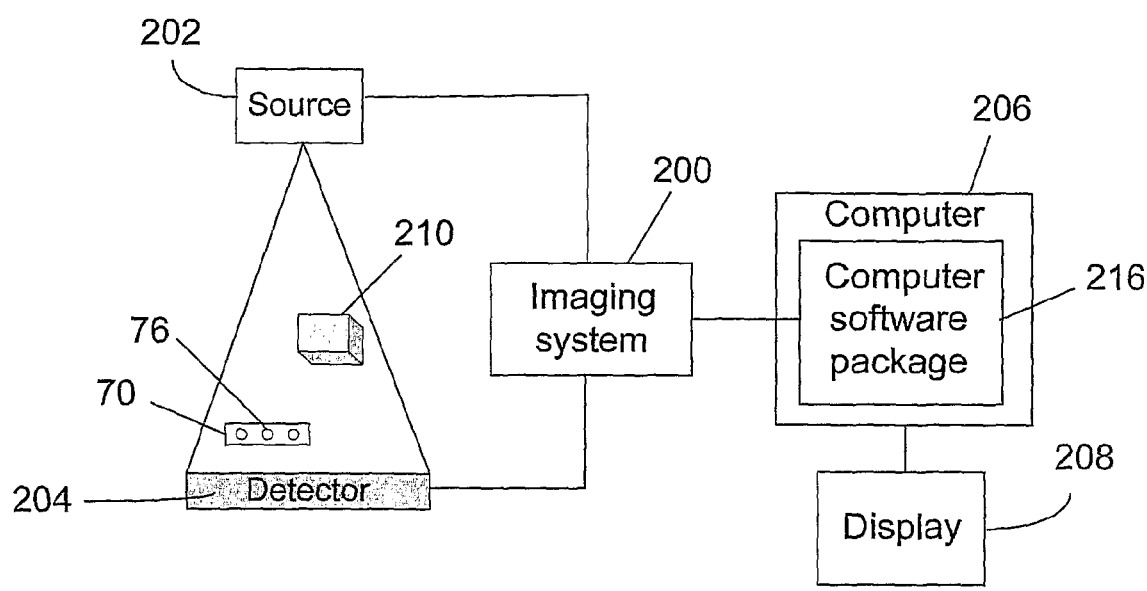
FIG. 16 symbolically shows how the system of the invention is integrated with an imaging system.

FIG. 16 symbolically shows how the system of the invention is integrated with an imaging system to improve the users understanding of the images produced with the imaging system. The essential components of imaging system 200 are the source of radiation 202 and the detector 204. The imaging system 200 is connected to a computer 206. When an at least partially opaque object 210 is placed in the space between the source 202 and detector 204 and system 200 is activated, object 202 blocks some of the radiation causing a shadow to appear on the detector. The output signals from detector 204 are sent to computer 206 where they are processed to produce images that can be stored in the memory of computer 206 and/or displayed on display device 208.

The system of the invention comprises two components: a calibration device 70, which is called a "ruler" herein and a computer software package 216. Radiolucent ruler 70 comprises radiopaque markers 76. It is placed in the space between source 202 and detector 204 such that at least some of the markers 76 will be visible in the images gathered by imaging system 200. Computer software package 216 is loaded into computer 206 in order to provide the computer with advanced capabilities for processing and displaying the images as a graphical overlay, displayed over the x-ray image on the display 206, thereby providing the user with information not previously available. Illustrative embodiments of the ruler and of the software as well as descriptions of the new types of visual information that can be provided to the user will be described herein below.

Herein the word "markers" is used to mean features that are visible in the image, by virtue of their color, luminance or intensity. In the case of x-ray images, markers have a different radio-opacity than their immediate surrounding, or comprise different radio-opacity levels. Markers are regarded as a singular point in space, e.g. the center of a ball or a corner of a cubical shape, which is well defined and can be noticed in the image. Herein the words "marker" and "feature" are used interchangeably.

In one embodiment, the ruler comprises two or more features having a known spatial relationship between them that are visible and recognizable in a radiographic image. For the purpose of the measurement the two or more features are aligned parallel to the measurement direction. The associated software allows, amongst many other modes of operation to be described herein, the automatic recognition of features of the ruler in the radiographic image and the use of these features to create a virtual extension of the ruler, i.e. to extend the ruler beyond its physical dimensions, and drawing the virtual extension on the image as an overlay. The invention enables the surgeon who is pointing the ruler and looking at the image to accurately measure dimensions of objects that appear in the radiographic image. The invention is especially useful and convenient for use with x-ray imaging in which frequently it is desired to measure the internal organs, bones, etc. of a body. However, as mentioned above, in principal the invention can be used with any technique of producing two dimensional images, e.g. regular photography.

All prior art methods known to the inventors use the physical scales on a ruler to measure the dimensions of or distances between objects of interest either directly or to take a picture and make the measurements directly on that picture in two dimensions. These methods are generally not accurate for the reasons mentioned hereinabove and do not enable easily measuring objects in different three dimensional orientations. The approach taken to the problem of making accurate measurements by the inventors is fundamentally different than that of the prior art since it makes use of control of both the tool, i.e. the ruler, and the display, i.e. the visual image including graphic overlay thereof. The measurement method is dependent on the combination of the ruler, which cannot be used to achieve the desired result when used alone and the software, which cannot, be used to make the measurements without the ruler. Only through the combination of ruler and software, as described hereinbelow can the desired result be obtained.

The invention, in its various embodiments, can be used to assist the operator in any procedure in which it is desirable or necessary to measure distances or dimensions of objects in radiographic images. Such procedures range from common chest x-rays, that are analyzed "off-line", to orthopedic and other surgical procedures that can only be carried out "on-line", i.e. with the aid of inter-surgery radiographic imagery using, for example, a mobile C-arm x-ray unit.

Typical non-limitative examples of on-line procedures that can be performed with the aid of the invention are:

Spinal fusion/lumbar spine fixation—insertion of pedicle vertebral screws;

Vertebroplastia—injecting cement to a vertebral body via the pedicles;

Bone biopsy—inserting a long needle through bone, to reach a tumor or lesion;

Dynamic hip screw (DHS) placement procedures for per-trochanteric and intertrochanteric hip fractures;

Three Cannulated Screws placement procedures for sub-capital fractures;

Proximal Femur Nail (PFN) placement procedures for oblique-reversed and for sub-troch hip fractures; and Trochanteric fixation nail (TFN) fixation.

For purposes of illustrating the invention, its use in relation to dynamic hip screw (DHS) placement procedures for hip trauma procedure under fluoroscopy will now be described. It is emphasized that the invention is not limited to use in any particular procedure and is expected to be useful for a wide range of applications. According to statistics made available by the American Association of Orthopaedic Surgeons, about 450,000 procedures for treatment of hip trauma were carried out in 2004. Nearly 90% of the procedures were carried out on persons aged 65 or older who had suffered breaks in the proximal end of the femur as a result of a fall. The surgical procedures for treating the fractures are well known and documented, including descriptions in textbooks, scientific journals, and even complete protocols that can be found on the internet. Generally speaking, depending on the exact nature of the break, the procedure involves attaching one of a number of different styles of commercially available compression hip plates to the femur by means of pins or screws inserted into holes drilled into the bone. A good review of the state of the art can be found in "Intertrochanteric Fractures" by Dr. Kenneth J. Koval and Dr. Robert V. Conto, which is a chapter in the book: Rockwood and Green's Fractures in Adults; Authors: Robert W. Bucholz, MD; James D. Heckman, MD; Publisher: Lippincott Williams & Wilkins; 6th edition, 2005.

A specific protocol for carrying out the surgical procedure can be downloaded from the web site of Smith & Nephew at [http://www.smithnephew.com/Downloads/71180375.pdf]

Figure 2:
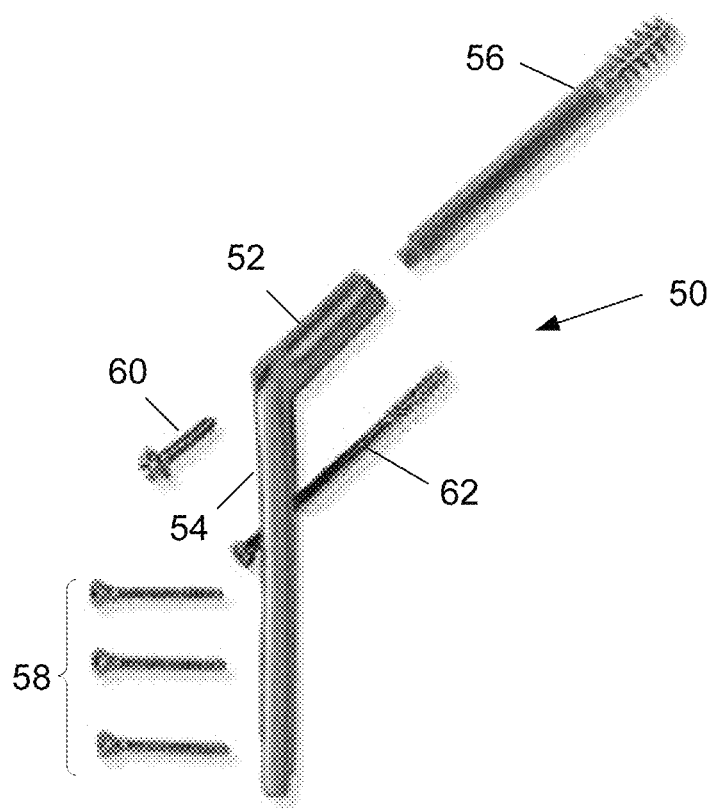
FIG. 2 shows a compression hip plate assembly.

FIG. 2 shows a compression hip plate assembly 50 manufactured by Smith & Nephew. The assembly comprises a plate 54 that fits against the outer surface of the femur with an attached barrel 52 that fits into a hole bored into the femur. After reduction and fixation of the fracture a hole is bored into the bone through the neck and into the head of the femur in order to attach lag screw 56. After lag screw 56 has been screwed into the head of the femur, the barrel is inserted into the hole, the plate is positioned on the side of the femur, and compression screw 60 is screwed in to attach the plate 54 to the lag screw and tightened to bring the broken pieces of bone together. Self tapping bone screws 58 are used to attach the plate firmly to the shaft of the femur and if necessary, depending on the type of break, cannulated or cancellous screw 62 can be inserted into the bone to capture medial fragments. There are hip plate kits available to the surgeon having many variations of the basic design. The variations include, for example, the length of lag screw 56, the angle between screw 56 and plate 54, and the number of cortical screws 58.

The most demanding part of the procedure is creating the hole into which the lag screw is inserted. For a successful procedure, the hole must pass through the bone in a path following the central axis of the neck of the femur towards the apex of the femoral head. The surgeon, assisted by a series of x-ray images taken during the course of the proceeding, uses a small diameter guide drill to make an initial guide hole. The first problem is to determine the neck angle to select an appropriate angle plate, which is used to help determine the proper entry point and to aim the guide drill. The surgeon, referring to the x-ray images, estimates the correct angle and entry point and begins to drill with the guide drill. After drilling a short distance into the bone, he stops and takes at least two x-rays at right angles to each other to ascertain that he is indeed drilling in the correct direction and along the center of the neck. In order to do this he must mentally project the image of the drill forward through the anatomical features, a task that is complicated, especially given the required precision and the challenging image quality. In addition, a typical C-arm equipped with an image intensifier tube for generating the images creates a distortion to the image usually causing straight lines to appear curved in the images: It is noted that if the surgeon has only to extend the line from the drill theoretically he is not influenced by the scale and a line in three dimensional world will still appear to be a line in the two dimensional projection image; however this theoretical extension is not an easy task, especially when precision is so important. If the drill path appears to be correct, then the surgeon drills a bit further before stopping to check again by repeated x ray imaging. If, at any stage, the path appears to be incorrect, then the surgeon must withdraw the guide drill and begin drilling again using a different angle and/or entry point. Another difficulty is ascertaining exactly where to stop drilling. It is essential that the lag screw be attached to as much of the bone as possible; however sufficient bone must remain at the apex of the head to prevent the lag screw from breaking through into the hip joint when the screw is inserted in the hole. This issue involves not only measurement of drilling orientation but also of drilling depth.

A typical procedure of this type carried out by an experienced surgeon takes a considerable amount of time, most of which is consumed by trial and error attempts to obtain the proper alignment. Additionally between 100-150 x-ray images are typically required, which, despite all precautions, represents a serious health hazard for both the patient and, to a greater extent, for the operating room staff that can be present for several similar operations each day.

Figure 3:
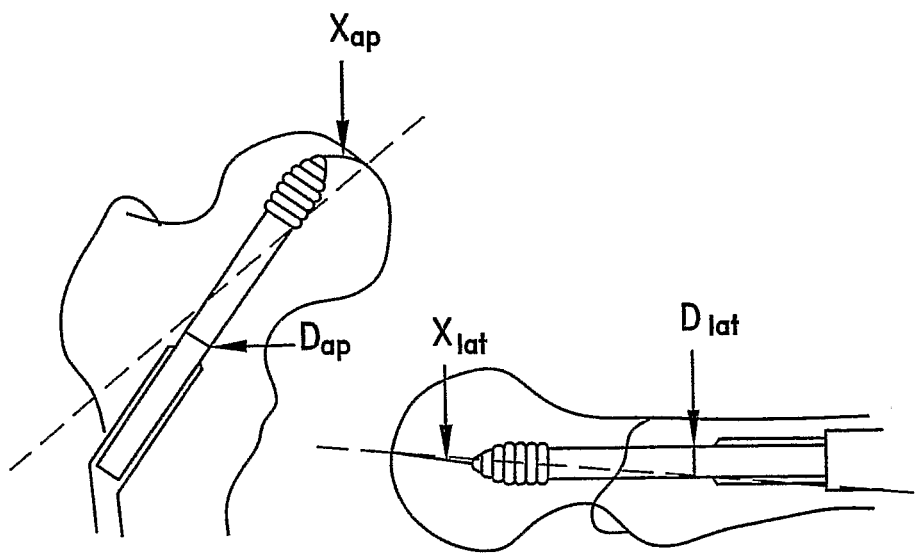
FIG. 3 illustrates the tip-apex distance (TAD)

The reason that so much time and care is taken to insure proper alignment of the guide hole is that failure of fixation of intertrochanteric fractures that have been treated with a fixed-angle sliding hip-screw device is frequently related to incorrect position of the lag screw in the femoral head. To insure success of the procedure and prevent mechanical failure, i.e. bone cut-out, an accuracy of ±2-3 mm of screw location is crucial. A simple measurement called the tip-apex distance (TAD) is used to describe the position of the screw. This measurement is illustrated in FIG. 3. The dashed lines represent the desired direction of the lateral axis of the lag screw in the radiographic images. $X_{ap}$ and $D_{ap}$ mark the distances from the tip of the lag screw to the apex of the femoral head and the measured diameter of the lag screw measured on an anteroposterior (AP) radiograph, respectively. $X_{lat}$ and $D_{lat}$ mark the same parameters measured on a lateral radiograph, and $D_{true}$ is the actual diameter of the lag screw. Then the TAD is given by the formula:

$$TAD = (X_{ap} \times D_{true}/D_{ap}) + (X_{lat} \times D_{true}/D_{lat})$$

The results of many studies show that the failure rate approaches zero if the TAD is less than 25 mm and the chances of failure increase rapidly as the TAD increases above 25 mm [M R Baumgaertner, S L Curtin, D M Lindskog and J M Keggi, "The value of the tip-apex distance in predicting failure of fixation of peritrochanteric fractures of the hip", The Journal of Bone and Joint Surgery, Vol 77, Issue 7, 1058-1064, 1995]. Using present techniques, the DHS can only be determined after the procedure has been completed. Using the present invention the surgeon will be able to estimate the DHS at the preplanning stage before beginning to drill the guide hole and will be able to know the expected value at any stage of the procedure.

Figure 4:
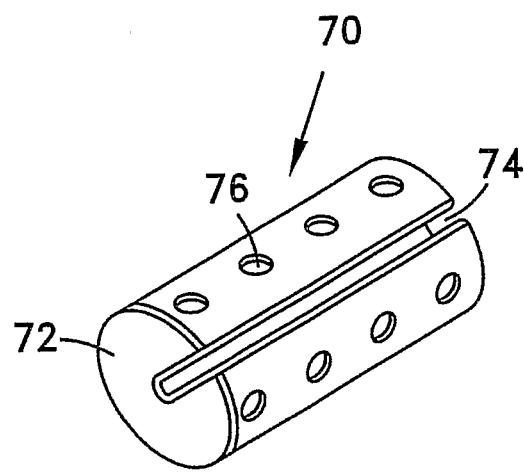
FIGS. 4, 5A and 5B illustrate two embodiments of one dimensional rulers of the invention.
Figure 5A:
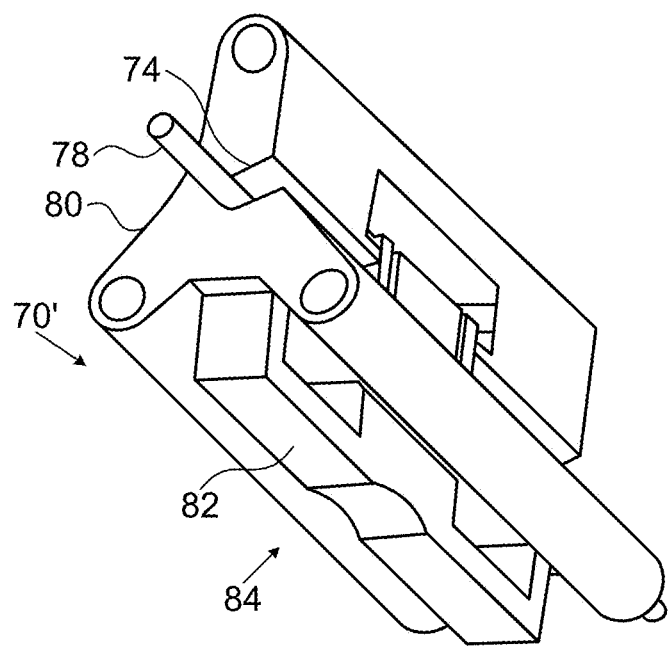
Figure 5B:
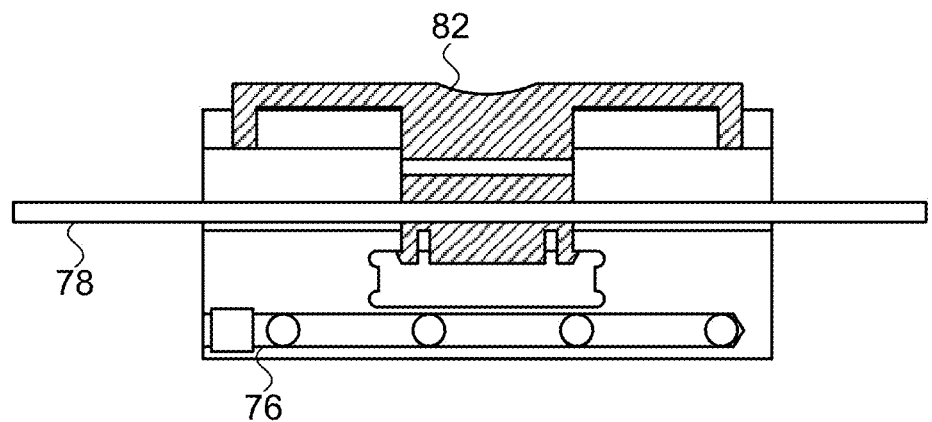

FIGS. 4, 5A, and 5B illustrate two embodiments of a one-dimensional ruler of the invention. In the embodiment shown in FIG. 4, ruler 70 is comprised of a cylinder 72 of radiolucent material. A slot 74 is created lengthwise in cylinder 72 so that the ruler can be slipped over the surgical tool, e.g. a guide, i.e. a thin bone drill sometimes known as a guide wire, without the necessity of releasing the guide from the power drill. The dimensions of the slot are such that the longitudinal axis of the guide and cylinder 72 coincide when ruler 70 is attached to the guide. The guide fits tightly in the slot so that the ruler will not slide freely but can be shifted easily by the surgeon to a new position when desired. Some embodiments of the ruler will rotate with the guide and other embodiments of the ruler can be attached so that the guide may rotate without rotating the attached ruler. Metal balls 76 are embedded into cylinder 72 in rows that are parallel to the direction of slot 74. Metal balls "floating" in a plastic cylinder are preferably used so that the x-ray signature of the ruler will be dark circles that are easily detectable in the image. One row of balls 76 is theoretically sufficient; however it is preferred that at least three rows of balls 76, equally radially spaced around the circumference of the base of cylinder 72, be used to insure that at any position of the ruler on the guide at least one row of balls will not be overlaid by the radiopaque guide or another row of balls, and will be visible on the x-ray image.

The exact distance between balls 76 is known so that when their shadows are detected on the x-ray image the dedicated software of the invention can identify them and measure the apparent distance between them directly from the image and use this measurement together with the known actual distance to calculate the scale that is used to create the overlays that allow the surgeon to determine the exact position of the guide relative to the anatomical structure, dimensions, and other related information displayed on a screen in "real time". As a minimum, only two balls 76 in one row are needed to be visible in the image in order to create an acceptable approximation of the C-arm magnification factor and the sizes of organs and tools for most common cases. However, since increased accuracy is obtainable by using the averages of several apparent measurements and also since some balls may be hard to see in the image it is preferred to use a minimum of three or four balls in each row to get a more accurate mathematical extension of the ruler. Also, if the angle between the ruler and the image plane is large, the scale change along the ruler extension, in the image, is not negligible. It is therefore preferred to use more than one measurement, at different heights, so that an approximation of this effect can be calculated.

Another way of explaining the problem of crating an accurate scale for the images and the solution to the problem is the following: It is known that the magnification increases linearly with the distance from the x-ray source. Therefore, if there are only two markers, the distance between them can be measured, however, it is impossible to determine if this distance is accurate because the ruler may not lie in a plane parallel to the image. Therefore, the measured distance between markers can not be counted on to provide an accurate scale for creating virtual extensions, overlays and other advanced features provided by the present invention. To overcome this problem a ruler with several markers, having a known distance between them, is used. If the ruler is parallel to the image plane, then the scale is correct and a true 2D calibration is obtained. If, however, the ruler is not parallel to the image plane, the distance between markers, i.e. the scale, will grow smaller to one direction and larger in the other direction, changing with the distance from the x-ray source. In this case, if there are three markers or more, not only the distance between markers but also the rate of change of the distance can be measured and therefore an accurate scale in both directions can be calculated.

FIG. 5A shows another embodiment of a ruler 70' of the invention. In this embodiment the radiolucent body 80 of the ruler is roughly a prism having an isosceles triangle as its base. The sides of the prism are cut away to leave a Y-shaped cross section. A row of metal balls 76 (seen in FIG. 5B, which is a cross-sectional view of ruler 70') is embedded at the apex of each of the arms of the "Y". A slot 74 is created along the longitudinal symmetry axis of body 80 of ruler 70'. Body 80 is slipped over guide 78 and then a clip 82 is attached to body 80 to hold guide 78 in slot 74. This can be done with the guide attached to the drill. In this embodiment the width of slot 74 need not necessarily be essentially equal to the diameter of the guide but it can be wide enough to allow the ruler to be attached to guides having a wide range of diameters. Clip 82 comprises a spring loaded brake (not shown) that locks ruler 70' in place, preventing it from sliding along guide 78.

Pressing downward on clip 82 in the direction of arrow 84 releases the brake allowing ruler 70' to be moved and repositioned along the guide. Repositioning can be easily accomplished by the surgeon using one hand, at any time during the procedure.

Figure 6:
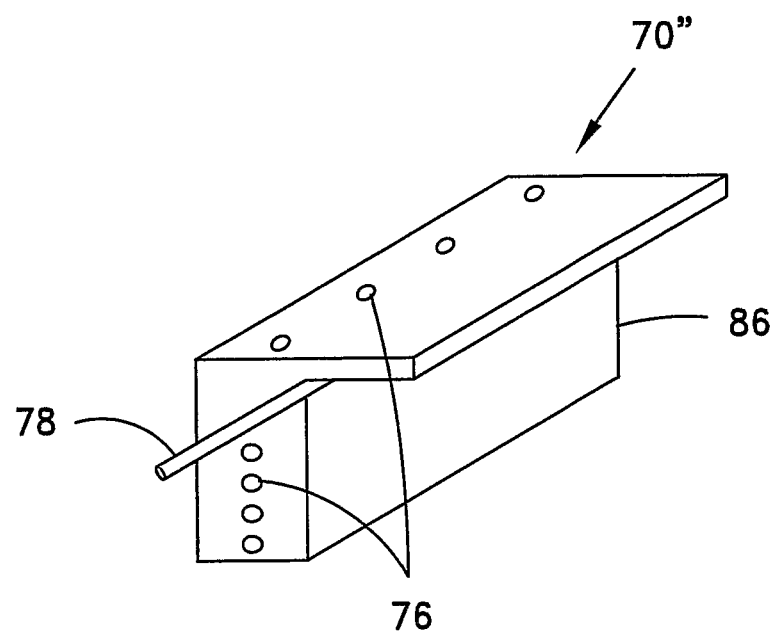
FIG. 6 illustrates an embodiment of a three dimensional ruler of the invention.

FIG. 6 illustrates an embodiment of a three dimensional ruler 70" of the invention. In this embodiment the radiolucent body 86 of the ruler has an "L" shaped cross section. Rows of radiopaque balls 76 are embedded in the walls of body 86. A suitable arrangement, e.g. a slit and/or a clip such as described above, are provided to slidingly hold ruler 70" in place on guide 78.

Many different arrangements of markers are described herein with regard to specific illustrative examples of the ruler. In principal the minimal requirement of the invention for the number and arrangement of markers is one of the following:

- Two markers aligned in the direction of the measurement—This will enable determining a scale with not very good accuracy because of the other degree of freedom described herein above.
- Three markers aligned in the direction of measurement—This will enable higher accuracy.
- A set of at least three markers, not on the same line, is sufficient in order to create an accurate three dimensional orientation and thereby enable measurement of an object in every orientation.
- In all cases, the markers do not have to be equally spaced but must be in a known spatial arrangement.
- In the figures herein several rows of equally spaced markers have been included so that they will not occlude each other and therefore allow a better chance of detecting them. There is, however, no minimal requirement of the number of rows of markers that must be used.

In another embodiment, the triangular sleeve with handle that is used by orthopedic surgeons to aid them in maintaining the alignment of the drill in a DHS placement procedure, as known to persons skilled in the art, can be modified by embedding a three dimensional ruler of the invention inside it, in which case, the modified sleeve itself can be used to fulfill the functions of the ruler of the invention that are described herein. The sleeve is made of radiolucent material and comprises a set of metal balls, arranged in a known spatial arrangement, such that the 3D orientation of the ruler may be calculated using the balls that appear in the image.

Figure 9A:
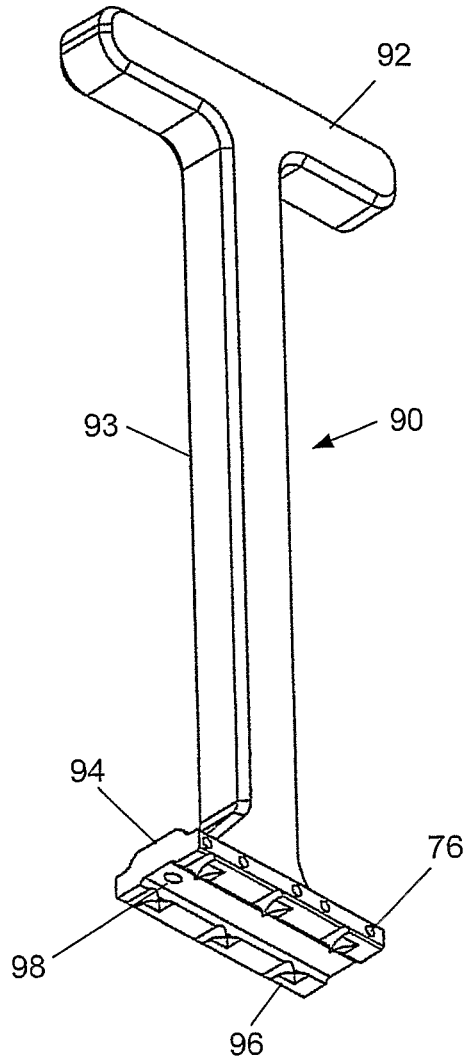
FIG. 9A to FIG. 9C show a handle comprising a ruler of the invention to be used by a surgeon to correctly align a drill guide.
Figure 9B:
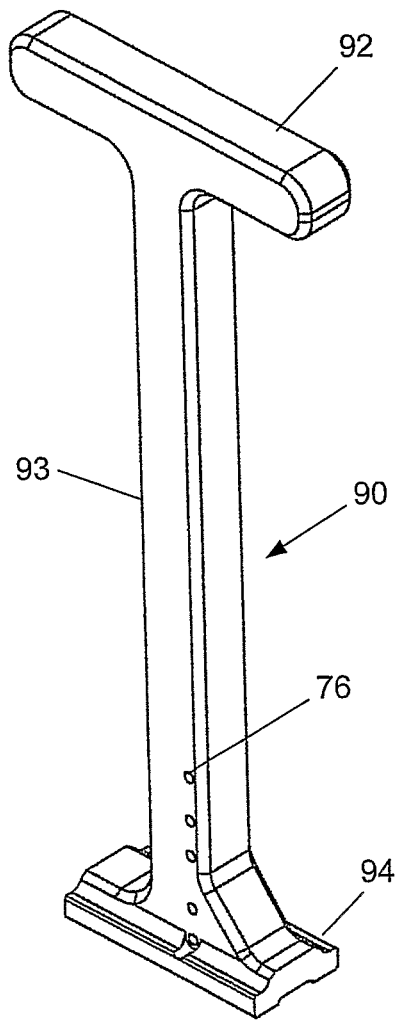
Figure 9C:
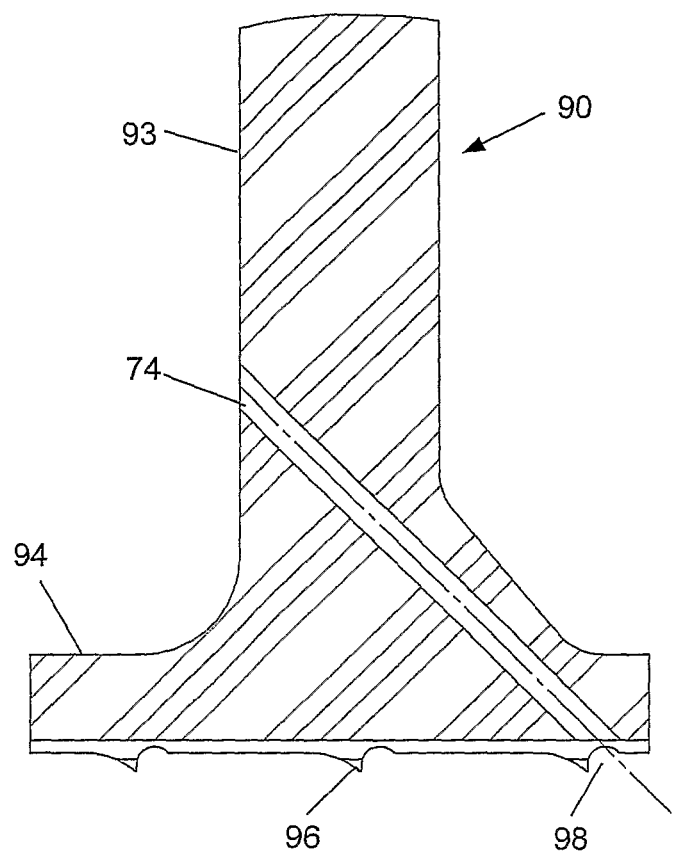

FIG. 9A to FIG. 9C respectively show front and back perspective views and a cross-sectional view of a handle 90 comprising a ruler of the invention that can replace the traditional triangular sleeve used by surgeons to aid in aligning a guide drill. As seen in the Figures, handle 90 has a "T" shape with a crosspiece 92 at the top of shaft 93 that allows the user to easily and firmly grip handle 90 with one hand. At the bottom of shaft 93 is a foot 94. The bottom surface of foot 94 comprises means, e.g. cleats 96, to prevent the device from sliding on the surface of the skin. In FIG. 9B the exit hole 98 of slot 74 (FIG. 9C) through which the guide drill passes can be seen on the bottom of foot 94. At least the foot 94 and the lower portion of shaft 93 (through which slot 74 passes) of handle 90 are made of a radiolucent material. In the illustrative example shown, embedded in this material are two rows comprised of five of radiopaque markers 76 each, a horizontal row embedded in the foot 94 and a vertical row embedded in the lower part of shaft 93. Notice that the markers in each row are not equally spaced and that neither of the rows of markers is aligned in parallel to the direction of the drilling. However, the software of the system can identify the markers 76 and from them determine the location and orientation of the handle 90, from this the exact orientation of slot 74, and can create a virtual extension of the guide that is inserted into slot 74, in the direction of drilling, beyond its physical dimension. Using this handle, a ruler need not be attached to the drill and the system of the invention will recognize the handle and can extrapolate it in both directions and can also display the implant template, i.e., a graphic overlay of where the implant would be, including all its parts, at the current position of the triangle (see, for example, FIG. 14 and FIG. 15). This approach allows an "intra-operative real time" visualization and measurement ability using the tools that are familiar to the surgeon.

In accordance with the discussion herein above, preferred embodiments of three dimensional rulers can be constructed comprising two sets of non-parallel rows of markers in order to provide a device for which the markers will be identified even when the ruler is partially occluded by other objects, e.g. bones or tools in the image. Using such a ruler, a three dimensional grid can be projected onto the image.

As discussed hereinabove, embodiments of the ruler of the invention comprise an elongated radiolucent body in which rows of radiopaque markers of known size and distance apart are symmetrically embedded. In its different embodiments, the ruler of the invention can be: a hand-held ruler used to "point: and "measure"; the ruler can comprise means for slideably attaching it to a surgical tool, e.g. handle 90 shown in FIGS. 9A to 9C; or the ruler can be an integral part of a surgical tool, possibly made by making at least part of the tool from a translucent material and embedding radiopaque markers into it. The ruler can be a one dimensional ruler in which the rows of radiopaque markers are parallel to the measuring direction or a three dimensional ruler in which a non parallel rows of markers are embedded. In some embodiments the ruler could comprise a metal comb or a metal jig, with no translucent material. The radiopaque markers would then be either characteristic features of the ruler, e.g. the teeth of the comb, or could be, e.g. metal balls attached to the body of the ruler.

Generally, when the ruler is attached to a surgical tool as will be demonstrated by example hereinbelow, during a medical procedure the ruler stays in a fixed position, e.g. at a location on the surface of the body or an organ within the body of a patient, while the tool is advanced into or withdrawn from the body or organ during the course of a diagnostic or surgical procedure.

In some preferred embodiments the ruler is made of bio-compatible USP class 6 materials and is reusable after sterilization using, for example, ETO. In a preferred embodiment, the entire ruler, except for the metal balls, is made of plastic. Under x-ray the ruler is seen as semi transparent and the metal balls are seen "floating" around the guide/drill. Based on these fundamentals and the examples of the embodiments described herein, skilled persons should have no trouble designing a ruler suitable for use with any diagnostic or surgical tool.

Figure 7:
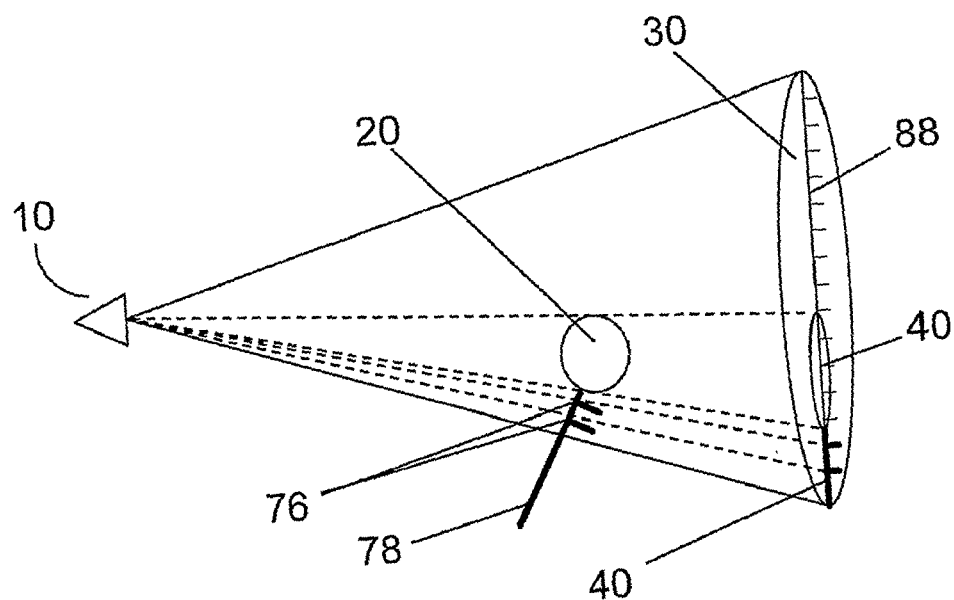
FIG. 7 and FIG. 8 schematically show respectively how one and two dimensional virtual extensions of the ruler of the invention are created overlaying the x-ray image of the object of interest.
Figure 8:
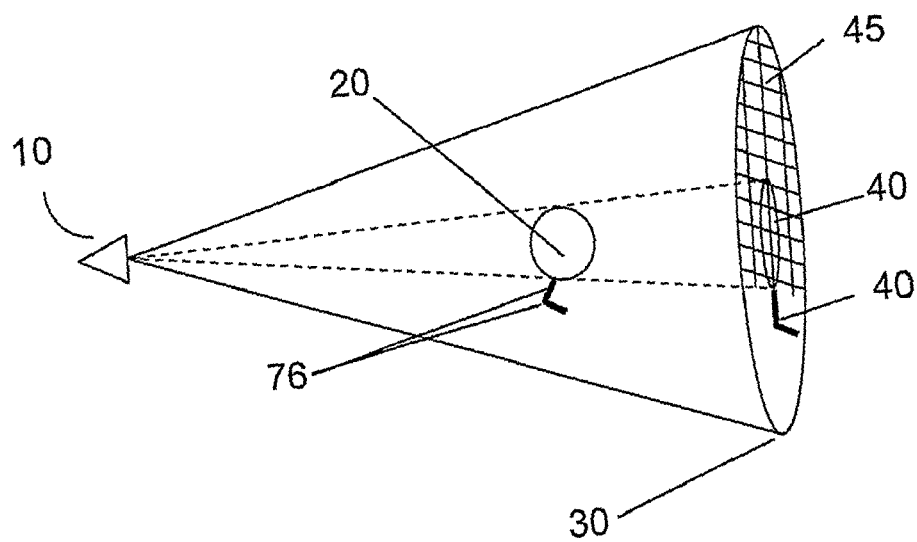

FIG. 7 and FIG. 8 schematically show respectively how one and two dimensional virtual extensions of the ruler of the invention are created overlaying the x-ray image of the object of interest. In FIG. 7, object 20 and radiopaque balls 76 embedded in a ruler of the invention, that is attached to guide drill 78, are shown positioned in the path of a beam of x-rays emitted by source 10. The dashed lines represent the shadows of the radiopaque objects that form images 40 on the electronic camera. The digital signals from the camera are processed using the software package of the invention to determine the distance between the images of the balls of the ruler. From the measured and known distances a scale factor is determined and a virtual extension 88 of the ruler is constructed. The virtual extension can be added as an overlay on the displayed x-ray image in a number of ways that can be selected by the operator. In the case of the orthopedic procedures described herein, the suggested display mode is to place the graphic presentation of the virtual extension exactly on top of the longitudinal axis of the guide drill with the origin at the distal tip of the drill, as seen in the x ray image. This is shown in FIG. 7 on the image plane representing the displayed image in the actual system. In this way, the surgeon can, using both forward distance scales and rearward distance scales, determine respectively how much farther the drill must be advanced and how far into the object the drill has penetrated.

Other display features are possible, e.g. color coding to easily distinguish between forward and rearward distances, the addition of transverse scales at locations selected by the operator to enable measurement of the distance from the center of the drill to the sides of the object for example to confirm that the hole is being drilled exactly through the center of the object, and the addition of color coded markings to indicate when the drill is approaching and/or has arrived at the location that drilling should cease.

FIG. 8 is similar to FIG. 7 with the exception that use of the three dimensional ruler provides sufficient information for the software to construct a two dimensional grid that can be displayed on the screen as an overlay on top of the x-ray image. In fact, since the three dimensional ruler can provide a complete three dimensional orientation, the grid could be drawn in any orientation, and not just the original orientation of the ruler (as shown in the Figure).

The system of the invention is used with a C-arm X-ray unit or some other imaging system. It comprises a ruler, and software that enables display of the virtual extension and allows display of the overlays and other features described herein, e.g. the software may include computer vision and recognition algorithms that are used to identify implants, surgical tools and anatomical features and to draw their counterparts or extensions during the operation as an overlay on the x-ray image (see FIG. 11). In some embodiments, the software works in semi-automatic mode wherein it allows the user to mark on the balls on the computer screen, e.g. by pointing to and clicking on them using a computer mouse, and then calculates the scale and draws the virtual extension. In other embodiments it is not necessary to mark all or some of the balls in an image or to mark the balls in successive images. The process may be started with a user click and then the software automatically searches for the markers and for the guide in the next image.

Skilled persons will recognize that the system can be given the ability to display the images in many different formats to assist the surgeon, e.g. different colors can be used to differentiate how far the drill has penetrated into the bone from the remaining distance. In addition, other types of information, can be provided by audible signal, e.g. signifying the remaining distance or when to stop drilling.

In addition, for imaging systems equipped with an image intensifier, some embodiments provide an anti-distortion system for extra accuracy. The anti-distortion system is a conventional one, as known to persons skilled in the art, comprises a grid placed on the image intensifier (the receiving end of the C-arm) and software that uses the image of the grid to correct the image obtained from the C-arm. Anti-distortion systems suitable for use with the present invention are described in: [Gronenschild E., "Correction for geometric image distortion in the x-ray imaging chain: local technique versus global technique" Med Phys. 1999, December; 26(12):2602-16]. In cases in which an anti-distortion system is used, the detection of the ruler markers using the software of the present invention has to be done on the image after the anti-distortion process.

Figure 17:
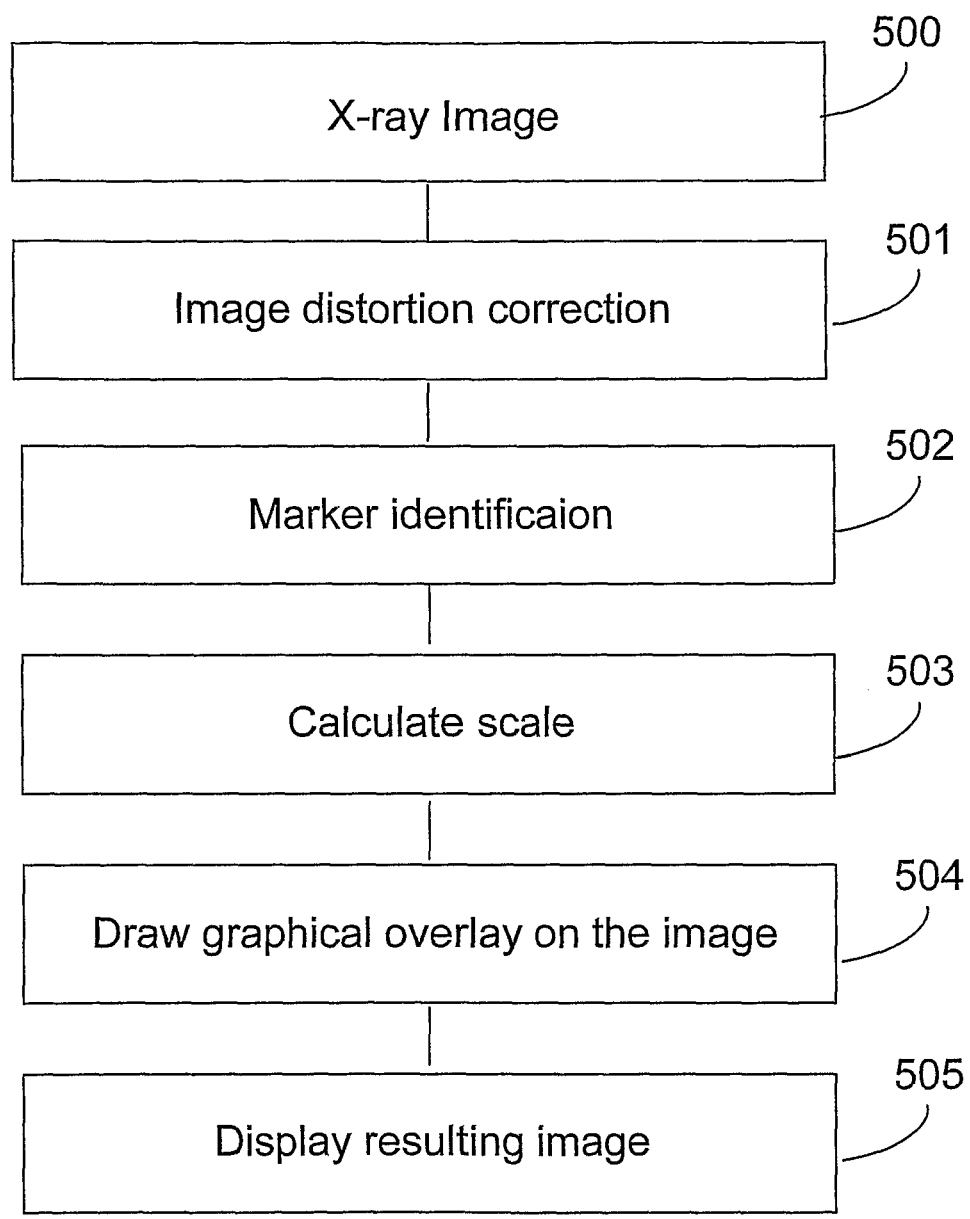
FIG. 17 is a flow chart outlining the main stages in processing and displaying the images using the system of the invention.

FIG. 17 is a flow chart outlining the main stages in processing and displaying the images using the system of the invention. In the first stage, 501, the x-ray image obtained using the imaging system 200 (see FIG. 16) undergoes an image distortion process. This phase is not mandatory, and depends on the imaging system. Some imaging systems do not create significant distortions and for these systems this phase can be skipped. Image distortion correction is done in any one of the standard ways, known in the art.

The next stage 502 is marker identification in the image. The marker, identification can be done either manually, where the user points at the location of the markers using a pointing device, such as a computer mouse; can be done in a semi-automatic manner, where some user input is required and some of the marker identification is done automatically; or can be done in a fully automatic manner, where an image processing algorithm, provided in the software of the system, is used to detect the markers in the image.

Figure 1A:
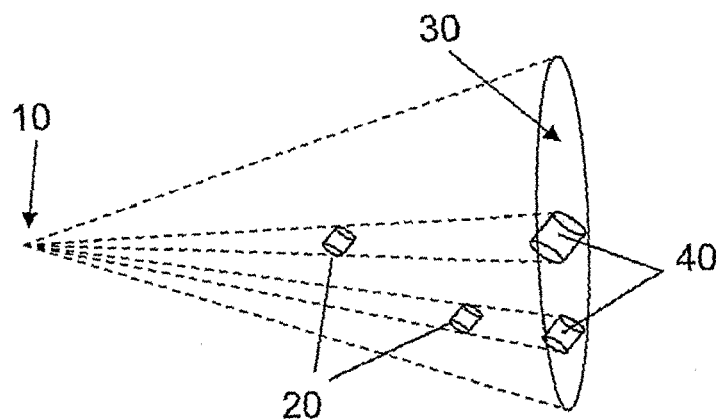
FIG. 1A and FIG. 1B illustrate the technical problem that is addressed by the present invention.
Figure 1B:
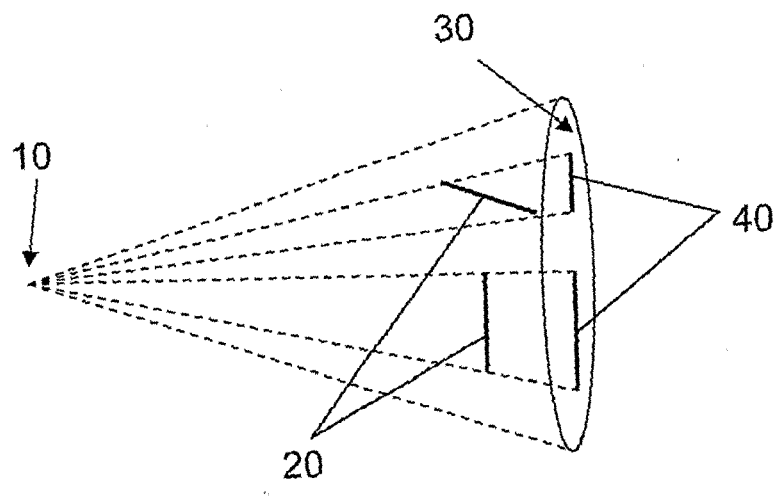

In the next stage 503, the software of the system calculates the scale, using the markers in the image identified in stage 502. If a one dimensional ruler has been used, then the markers are co-linear and the only scale that can be deduced is in the direction of the markers. Since the magnification of an object depends on its distance from the x-ray source, if only two markers are used, the exact position and orientation of the ruler cannot be determined, since a rotation of the ruler may have the same effect, as a change of distance from the x-ray source, on the distance between the markers on the image (see FIGS. 1A and 1B). Since the orientation of the object is not determined, ruler extrapolation cannot be achieved with high accuracy because, if the measurement direction is at an acute angle to the x-rays, scaling changes rapidly along the direction of measurement. In order to be able to extrapolate the ruler accurately, it is necessary to have at least three markers on the line, in which case the scale as well as the orientation of the measurement direction can be calculated with respect to the x-ray image, since the scale linearly increases with the distance from the x-ray source. If the user is willing to ignore this magnification problem, a less accurate approximation may be obtained using only two markers.

When using a three dimensional ruler objects can be measured at any orientation. The minimal requirement in the three dimensional case is at least 3 markers that are not co-linear.

In the next step 504 the system draws an overlay over the x-ray image. The overlay may include any type of graphical or other information, drawn or printed over the image. Amongst other things, it may include a virtual extension of a drill, an implant image, taken from a pre-stored library of implants, or a virtual drawing of a measurement ruler, aligned with the device. The overlay can make use of the location and orientation of the device in the image. Preferred embodiments may include a GUI that enables the user to easily select and customize the overlay shown over the images.

Figure 15:
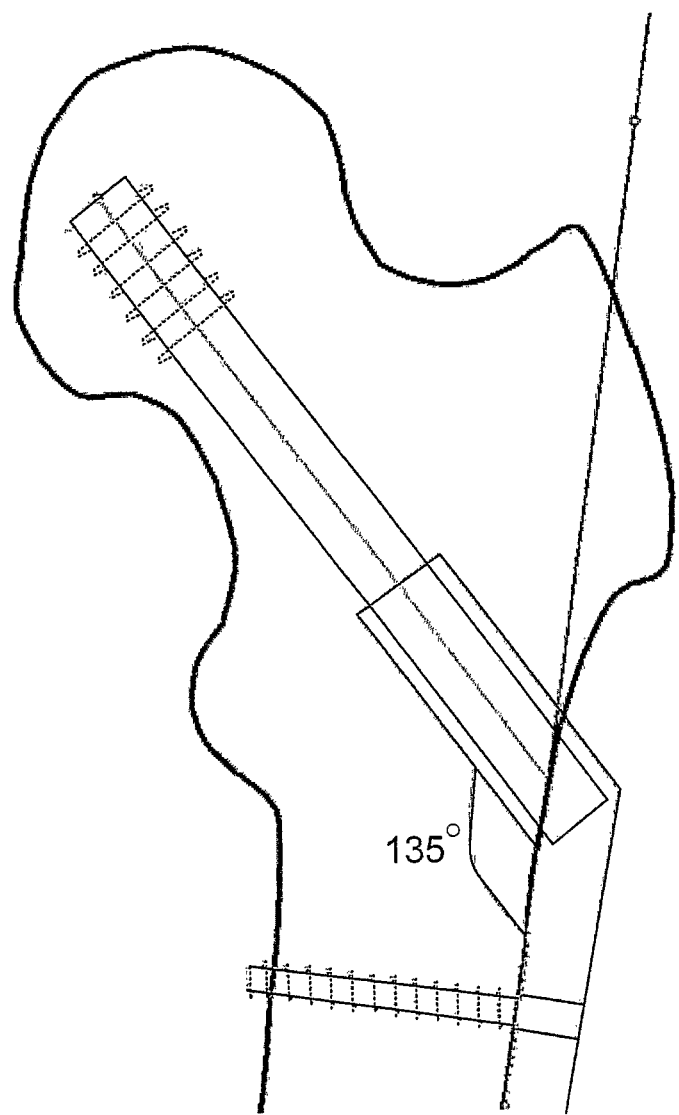

The use of the invention and its advantages will now be demonstrated with reference a dynamic hip screw (DHS) placement procedure. The entire procedure is carried out in the operating room with the aid of a C-arm x-ray system. After completing the fracture reduction the surgeon begins the pre-operative planning. This stage is carried out before sterilization and cutting the skin to expose the bone. The common practice is to take one image from approximately an anterior/posterior (AP) angle, and do the entire operation planning on a single image while ignoring the three dimensional aspects of the bone. Since embodiments of the invention can be used to identify the surgeon's tools and draw their virtual extension, e.g. the track that a drill will follow, such embodiments can be used during the planning stage. The surgeon can attach a ruler, e.g. ruler 70 (FIG. 4) to the distal end of the guide drill or slide the guide drill into the slot of a handle, e.g. handle 90 (FIG. 9A), place the distal end of the guide drill against the outside surface of the skin, and point the guide in the direction he wishes to drill. The software of the system will then draw the virtual extension of the ruler and overlay it on the x-ray image thereby helping the surgeon to optimize the determination of penetration point and drilling angle and measure how deep he should drill. In some embodiments the software package of the invention enables the surgeon to apply templates of the tools and lag screws of different dimensions and to determine accurate measurements of the anatomical features to plan exactly the operation, including screw selection, and to visualize the end result. FIG. 15 shows this feature of the operation planning stage.

Figure 12:
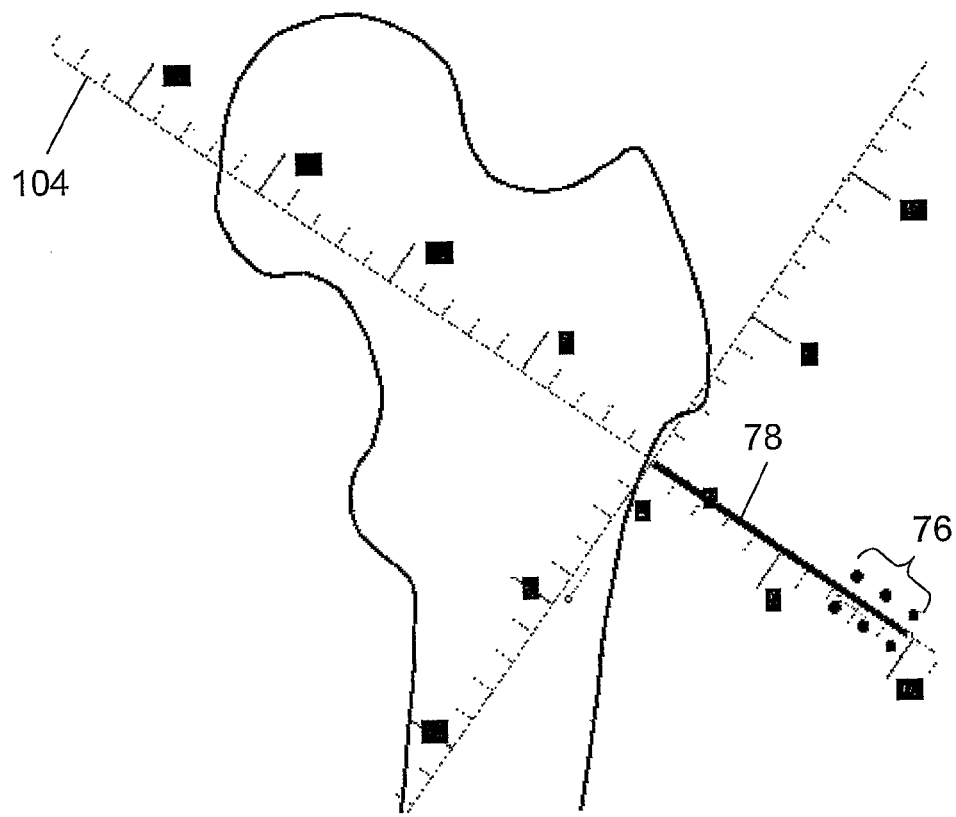

FIG. 12 shows the display during operation, after the skin was already cut and some of the surgical tools were inserted to the body. The drill 78 is about to enter the femur and the surgeon uses a triangular sleeve to enter at the correct angle (135 degrees). On top of this image a two dimensional grid has been drawn to illustrate how the ruler of the invention and its virtual extension 104 would appear.

Figure 13:
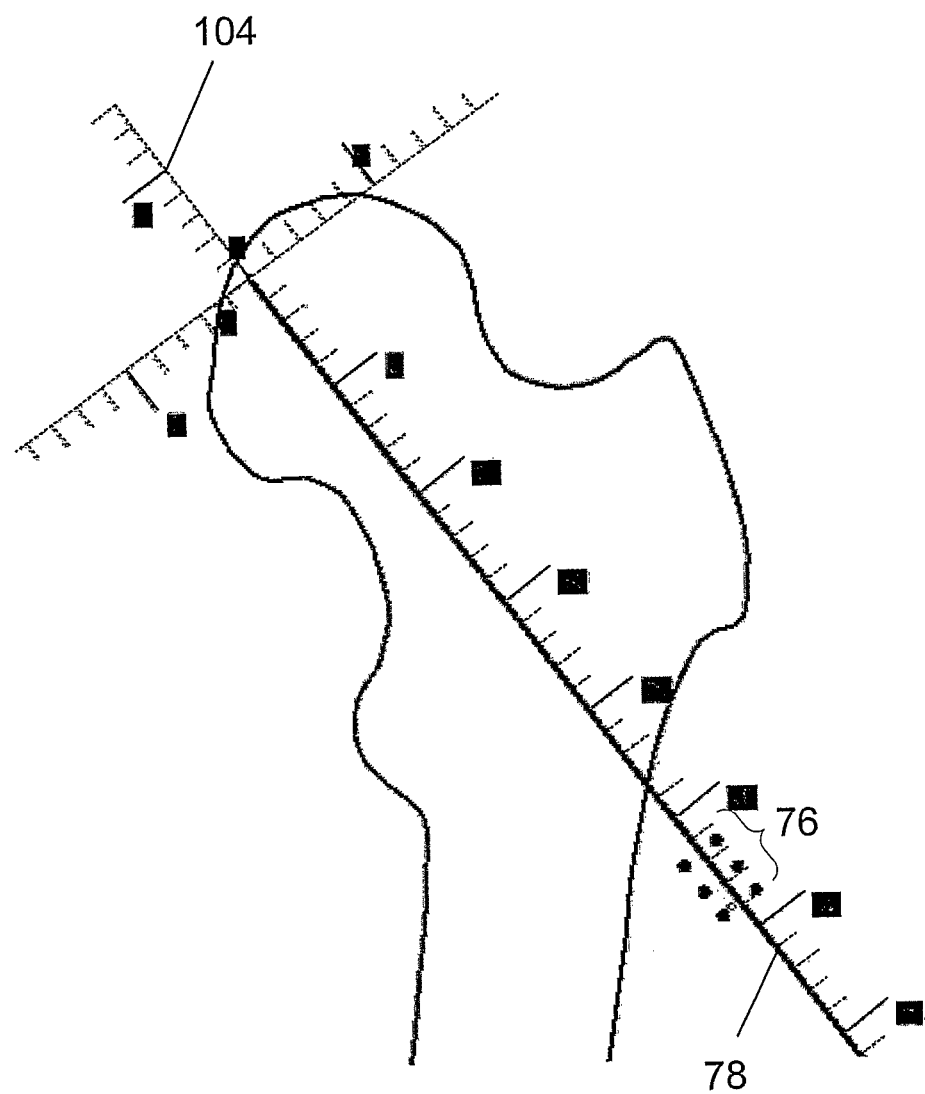

FIG. 13 shows the situation after drilling with the guide drill 78. The virtual ruler 104 displayed on the screen overlaying the guide and the bone allows the surgeon to see exactly how far the drill has penetrated the bone and to confirm that the path is correct. In order to achieve maximum accuracy a three dimensional ruler is used to determine the plane on which to draw the line perpendicular to the drilling direction, i.e. to correct for the change of scale of the ruler on the drill caused by the fact that the drill is tilted at an angle relative to the plane of the image. In most cases a one dimensional ruler could be just as useful; but in either case, the surgeon can see how far the guide tip is from the hip joint. This is useful for determining the expected distance from the joint. Note that this is not exactly the tip apex distance, but rather a more accurate 3D measurement, that is similar in concept to the TAD.

After the screw has been installed in the bone, the virtual ruler allows the surgeon to accurately measure the tip-apex distance and verify that the surgery has been performed properly.

Figure 10A:
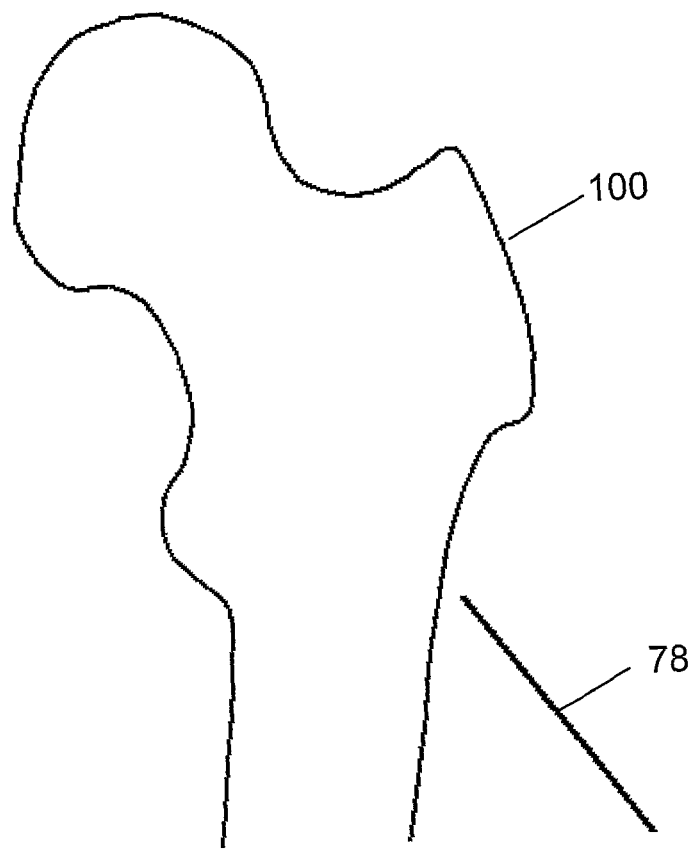
FIG. 10A to FIG. 15 illustrate some of the modes of operation of the system of the invention.
Figure 10B:
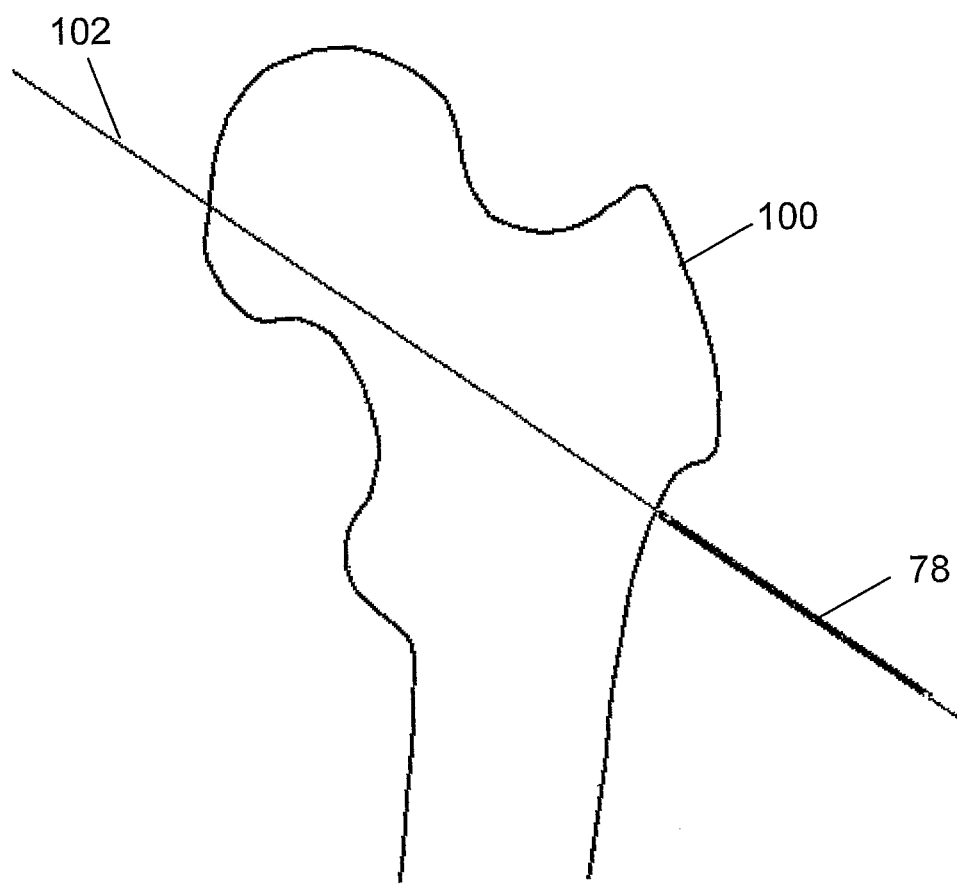

As is apparent from the description hereinabove, embodiments of the invention are very versatile when applied to orthopedic surgery and the software package may have the capability of allowing the operator to choose from many different operating modes, depending on the requirements or stage of the procedure. A list of some prominent modes of operation, some of which are shown schematically in FIG. 10A to FIG. 15, will now be presented:

1. Virtual extension of a tool or object in an image - This mode of operation can be carried out by the system of the invention using an image recognition program included in the software package without the use of the ruler or any other sensors. FIG. 10A is a drawing showing the guide drill 78 brought close to the femur 100. FIG. 10B shows guide 78 in contact with femur 100. The software of the system of the invention, at a command from the operator, recognizes the guide in the x-ray image and draws its virtual extension (thin line 102) through the bone. This allows the surgeon to easily see the path that the drill will follow through the bone and correct it, if necessary, before starting to drill.

2. Virtual extension of the ruler—The pointing aspect of the ruler of the invention is essentially different from image calibration or normal rulers. The system extends the ruler so that the operator only needs to look at the image, which also shows the ruler, and to point the ruler in the direction he wants to measure in order to get the measurement. The zero scale on the ruler of the virtual extension can be dragged and moved around on the image at will, thereby making it easy for the operator to make any measurement that he feels is necessary. Note that in prior art calibration techniques the points the operator wishes to measure must be marked on the image and the calibration device moved to measure between the points.

The pointing aspect is especially important in measuring objects in live video since in this case the operator can't take the time to mark the points of interest. An example of such a measurement is to measure the size of the heart under x-ray while injecting a contrast liquid to the blood.

Figure 11:
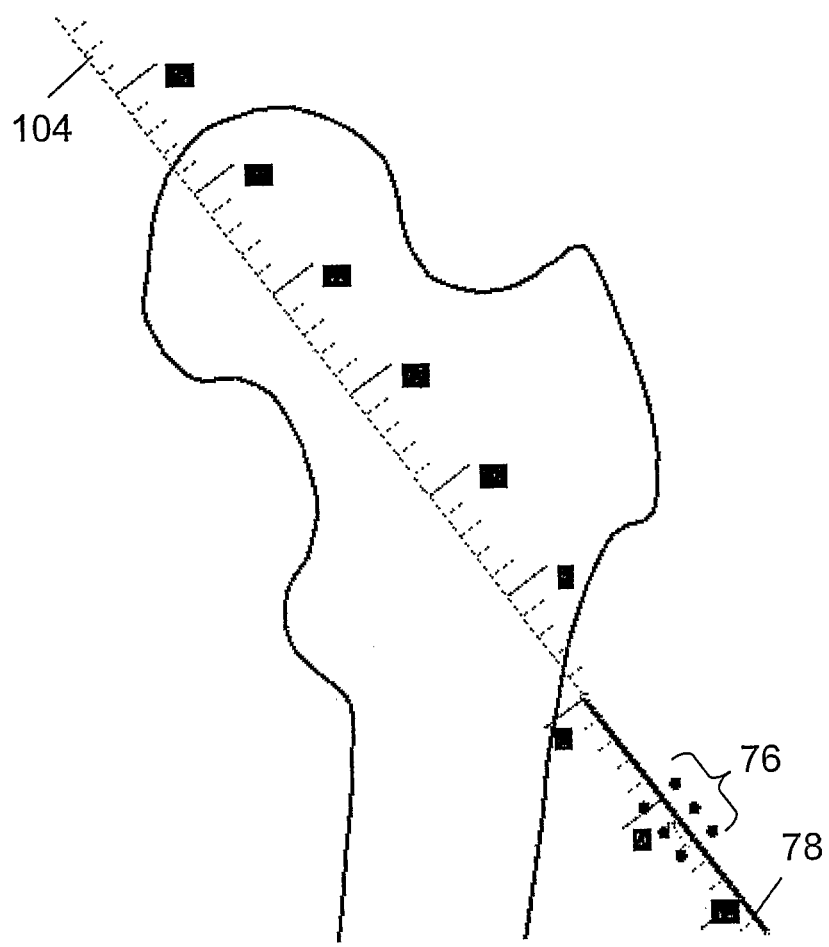

FIG. 11 shows how a surgeon would use the virtual extension 104 of a one dimensional ruler 76, mounted on a guide 78, to measure how deep he wants to drill. FIG. 12 shows how a surgeon would use the virtual extension of a three dimensional ruler 76, mounted on a guide 78, to measure the distance from the insertion point of the drill, in the direction of drilling.

3. Using one or three-dimensional rulers to project accurate grids on the image. FIG. 13 shows how a surgeon would use the virtual extension 104 of a three dimensional ruler 76, mounted on a guide 78, to measure the distance from the hip joint, both in the direction of drilling, and in the direction perpendicular to it. This is not exactly the tip-apex distance, but a more accurate 3D measurement that was not possible in the prior art, and is similar to the TAD.

4. Projecting approximate grids on the image. For example, working with a one dimensional ruler the software simply assumes that the other axes have a similar scale.

5. Real time visualization—This has two aspects: Use either a one or a three dimensional ruler in order to draw how the result of the operation (or part of it) will look given the positioning of the ruler or some other surgical tool. For example, if it is decided to drill in a particular direction, the system of the invention can show how the DHS will be positioned. The other aspect, based on mode 1, is to simply use an approximate dimensional scale based on the known or approximate dimensions of the objects seen in the image to create the grids. This may be inaccurate and spatially wrong, but can sometimes be good enough. For example, it is enough to see a guide drill in the image to know the approximate scale of the image and draw the DHS screw or the entire DHS implant around it.

Figure 14:
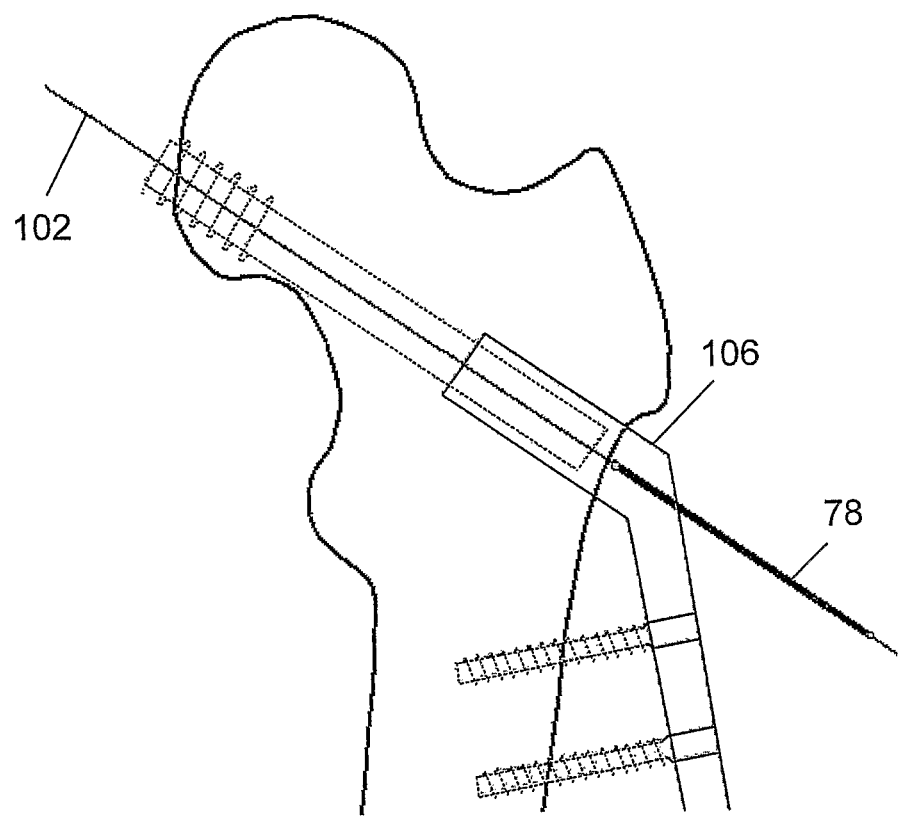

Real time visualization takes place after the planning stage, during the actual procedure itself. FIG. 14 illustrates this mode of operation. After fracture reduction the surgeon cuts the skin and brings the tip of the guide drill 78 into contact with the bone. He then takes an x-ray image and asks the system of the invention to draw a virtual extension 102 of the guide on the image. As a result of the pre-operation planning step (described herein below) he knows which DHS assembly to use. He now requests that the system of the invention retrieve the template 106 of the selected DHS assembly and draw it around the extension 102 of the guide 78. Note that in FIG. 14, the guide has been deliberately placed in a wrong direction of drilling and a wrong entry point in order to demonstrate how drawing the template on the guide can be helpful for the surgeon, i.e. having the template drawn on the image makes it very easy for the surgeon to see that he/she is/or is not drilling in the right place/direction.

6. Pre-operative planning—FIG. 15 illustrates this mode of operation. This mode is carried out on an image taken after the fracture reduction, using a calibration and a template library. Here the surgeon chooses different templates and has them drawn, i.e. overlaid, on the image of the bone to determine exactly which DHS assembly has the proper parameters to use with the specific bone and how to place it. Note that this is very different from the instant visualization, although sometimes the images look similar. Also, although operation planning is not new, the inventors are not aware of any other computerized system that enables the planning to be done inside the operating room. In trauma cases, the planning has to be done in the operating room since only after fracture reduction can the operation be planned.

7. Image enhancement—The processing means of the system automatically determines the location of the guide in the image, therefore an image enhancement algorithm can be applied that automatically concentrates on the specific area of interest to the surgeon.

8. Synchronizing AP/axial images—This is one of the most demanding tasks facing surgeons performing surgical procedures under guidance of a c-arm system. Consider a dynamic hip screw (DHS) placement procedure and suppose that the surgeon, using the system of the invention, first takes an image I from an axial angle, with a ruler on a guide. Then, without moving the guide, he takes another image J from AP angle. If afterwards he drills a bit more and then takes a third image K, also from an AP angle, then the system can calculate how deep the drill got in image I. This is only possible since the ruler is visible on all the images I, J, and K and is done by measuring the true distance of drilling between J and K, and virtually extending the drill by that distance in image I.

This is a very important feature that can save the surgeon the difficulty of going back to the axial angle and taking another image. This means less radiation and less operating time, and instant feedback.

It is to be noted that in certain applications the known shape and dimensions of surgical tools or even anatomical features that are visible in the x-ray image can be used in place of a ruler. In these cases the methods described above can be used to produce the same visual effects described hereinabove; e.g. virtual extension of the tool or placement of a template on a bone.

Although embodiments of the invention have been described by way of illustration, it will be understood that the invention may be carried out with many variations, modifications, and adaptations, without exceeding the scope of the claims.

The invention claimed is:

1. A system for measuring the true dimension and orientation of objects in a two dimensional(2D) medical image, said system comprising:
a set of markers visible in the 2D medical images, which markers are located upon a surgical tool and have known spatial relationships between them;
receiving circuitry adapted to receive a given 2D medical image, which given 2D medical image includes the surgical tool and an organ of a subject;
image processing circuitry adapted to calculate distance within the given 2D image based on the appearance of said markers in the 2D image, characterized in that said processing circuitry include programs adapted to:
(a) identify said markers in the given 2D medical image and determine their location;
(b) calculate from the determined locations of the identified markers in the given medical image a three dimensional position and orientation of the surgical tool, in relation to the organ, thereby providing 3D positional information of the tool from the appearance of the markers in the given 2D medical image; and
(c) calculate a dimension of a spatial relationship between the surgical tool, or a point on the surgical tool, and the organ, based on the locations of the identified markers in the given medical image and the calculated relative 3D position and orientation of the surgical tool.

2. The system according to claim 1, wherein the organ is a femur.

3. The system according to claim 1, wherein the given 2D medical image is a radiographic image.

4. The system according to claim 1, wherein the dimension is a tip-apex distance.

5. The system according to claim 1, wherein the image processing circuitry is further adapted to identify a contour of the organ in the given 2D medical image.

6. The system according to claim 2, wherein the image processing circuitry is further adapted to identify a contour of a head of the femur in the given medical image.

7. The system according to claim 5, wherein the dimension is a distance between a point on the surgical tool and a point on the identified contour of the organ.

8. The system according to claim 1, further comprising a rendering module adapted to render upon the given medical image an overlay of an implant, positioned in relation to the organ based on a prediction of an expected location of the implant considering the current determined 3D position and orientation of the surgical tool.

9. A system for measuring the true dimensions and orientation of objects in a two dimensional (2D) medical image, said system comprising:
a set of markers visible in the medical images and having known spatial relationships between them, which markers are located upon a penetrating surgical tool, wherein the penetrating surgical tool has a penetrating tip for penetrating human tissue;
receiving circuitry adapted to receive a given 2D medical image, which given 2D medical image includes the surgical tool and an organ of a subject;
image processing circuitry adapted to render an extension of the penetrating tip upon the given 2D medical image;
characterized in that said image processing circuitry comprises image processing logic that allows said image processing circuitry to identify the markers in the given 2D medical image and use said identified markers to create a virtual extension of the penetrating tip of the penetrating surgical tool, thereby enabling a user to accurately predict a trajectory of the penetrating tip and to draw the virtual extension of the penetrating tip, on the 2D medical image, as an overlay.

10. The system according to claim 9, wherein the organ is a femur.

11. The system according to claim 9, wherein said image processing circuitry is further adapted to determine a distance between the penetrating point and a point on the organ.

12. The system according to claim 11, wherein the distance is a tip-apex distance.

13. The system according to claim 9, further comprising automatically identifying, by the processing circuitry, a contour of the organ in the given 2D medical image.

14. The system according to claim 10, further comprising automatically identifying, by the processing circuitry, a contour of a head of the femur in the given 2D medical image.

15. The system according to claim 13, wherein said image processing circuitry is further adapted to determine a distance between the penetrating point and a point on the identified contour of the organ.

16. The system according to claim 9, wherein said image processing circuitry is further adapted to render upon the given 2D medical image an overlay of an implant, positioned in relation to the organ based on a prediction of an expected location of the implant considering the current determined 3D position and orientation of the surgical tool.

17. A system for measuring the true dimension and orientation of objects in a two dimensional (2D) medical image, said system comprising:
a set of markers visible in the 2D medical images and having known spatial relationships between them;
receiving circuitry adapted to receive a given 2D medical image, which 2D medical image includes the markers, a surgical tool and an organ of a subject;
image processing circuitry adapted to calculate distance within the given 2D image based on the appearances of said markers in the 2D image;
characterized in that said processing circuitry includes programs adapted to:
(a) identify said markers in the given 2D medical image and determine their location;

(b) calculate from the determined location of the identified markers in the given medical image a three dimensional position and orientation of the surgical tool, in relation to the organ, thereby providing 3D positional information of the tool from the appearance of the markers in the given 2D medical image; and (c) calculate a dimension of a spatial relationship between the surgical tool, or a point on the surgical tool, and the organ, based on the locations of the identified markers in the given medical image and the calculated relative 3D position and orientation of the surgical tool.

18. The system according to claim 17, wherein said image processing circuitry is further adapted to determine a trajectory of the surgical tool and render the trajectory upon the given 2D medical image.

19. The system according to claim 17, wherein the dimension is a tip-apex distance.

20. The system according to claim 17, further comprising a rendering module adapted to render upon the given 2D medical image an overlay of an implant, positioned in relation to the organ based on a prediction of an expected location of the implant considering the current determined 3D position and orientation of the surgical tool.

21. A system for measuring the true dimensions and orientation of objects in a two dimensional (2D) medical image, said system comprising:

a set of markers visible in the 2D medical images, which markers are located upon a surgical tool and have known spatial relationships between them;

receiving circuitry adapted to receive a given 2D medical images, which given 2D medical image includes the markers and an organ of a subject;

image processing circuitry adapted to calculate distances with the given 2D image based on the appearances of said markers in the 2D image; characterized in that said processing circuitry includes programs adapted to:

(a) identify said markers in the given 2D medical image and determine their location;

(b) calculate from the determined location of the identified markers in the given medical image a three dimensional position and orientation of the surgical too, in relation to the organ, thereby providing 3D positional information of the tool from the appearance of the markers in the given 2D medical image; and (c) calculate a dimension of a spatial relationship between two points on the organ, based on the locations of the identified markers in the given 2D medical image.

22. The system according to claim 21, further comprising a rendering module adapted to render upon the given 2D medical image an overlay of an implant, positioned in relation to the organ based on a prediction of an expected location of the implant considering the current determined 3D position and orientation of the surgical tool.

23. The system according to claim 21, wherein the given 2D medical image is a radiographic image.

24. The system according to claim 21, further comprising a rendering module adapted to render, intra-operatively, upon a display, the given 2D medical image along with the calculated dimension, wherein the given 2D medical image was acquired intra-operatively.

\* \* \* \* \*